(12) United States Patent
Fessler et al.

(10) Patent No.: US 10,213,234 B2
(45) Date of Patent: Feb. 26, 2019

(54) INTERSPINOUS PROCESS FIXATION DEVICES, SYSTEMS, INSTRUMENTS AND METHODS OF ASSEMBLY AND USE

(71) Applicant: IN QUEUE INNOVATIONS, LLC, Winona Lake, IN (US)

(72) Inventors: Richard G Fessler, Winnetka, IL (US); John W Boger, Saratoga Springs, NY (US)

(73) Assignee: IN QUEUE INNOVATIONS, LLC, Winona Lake, IN (US)

( * ) Notice: Subject to any disclaimer, the term of this patent is extended or adjusted under 35 U.S.C. 154(b) by 0 days.

(21) Appl. No.: 15/264,099

(22) Filed: Sep. 13, 2016

(65) Prior Publication Data
US 2016/0374733 A1   Dec. 29, 2016

Related U.S. Application Data

(63) Continuation of application No. PCT/US2015/020520, filed on Mar. 13, 2015.
(Continued)

(51) Int. Cl.
| | | |
|---|---|---|
| *A61B 17/16* | (2006.01) | |
| *A61B 17/70* | (2006.01) | |
| *A61F 2/30* | (2006.01) | |

(52) U.S. Cl.
CPC ...... *A61B 17/7068* (2013.01); *A61B 17/1622* (2013.01); *A61B 17/1631* (2013.01);
(Continued)

(58) Field of Classification Search
CPC ....... H04B 1/7156; H04B 2001/71563; H04W 72/0453; A61F 2/4405; A61B 17/7065;
(Continued)

(56) References Cited

U.S. PATENT DOCUMENTS 9,717,540 B2 * 8/2017 Robinson ........... A61B 17/7068
2008/0281359 A1   11/2008 Abdou
(Continued)

FOREIGN PATENT DOCUMENTS

CN      201248758    *   6/2009   ......... A61B 17/7068
CN      201248758 Y       6/2009
(Continued)

OTHER PUBLICATIONS

International Search Report and Written Opinion issued for International Application No. PCT/US2015/020520 dated Aug. 3, 2015.
Extended European Search Report and Search Opinion issued in European Application No. 15761009.8 dated Oct. 16, 2017.

*Primary Examiner* — Pedro Philogene
(74) *Attorney, Agent, or Firm* — Heslin Rothenberg Farley & Mesiti P.C.; Jacquelyn A. Graff

(57) ABSTRACT

The present invention discloses spinous process fixation devices, systems, and instruments. The spinous process fixation device includes a first member, a second member, a third member, and a fourth member. Each of the first and second members includes a body and an engagement member and the engagement member of the first member couples to the engagement portion of the second member. Each of the third and fourth members also includes a body and an engagement member and the engagement member of the third member couples to the engagement portion of the fourth member. A method of assembling the spinous process fixation device and methods of using the spinous process fixation devices are also disclosed. A reamer instrument is also disclosed.

16 Claims, 24 Drawing Sheets

Related U.S. Application Data

(60) Provisional application No. 61/953,720, filed on Mar. 14, 2014.

(52) U.S. Cl.
CPC ...... *A61B 17/1671* (2013.01); *A61B 17/7065* (2013.01); *A61F 2002/305* (2013.01); *A61F 2002/30504* (2013.01); *A61F 2002/30505* (2013.01); *A61F 2002/30599* (2013.01)

(58) Field of Classification Search
CPC ............ A61B 17/7068; A61B 17/7062; A61B 17/7061; A61B 17/7064; A61B 17/1671; A61B 17/1631; A61B 17/1622; A61B 2002/4475; A61B 2002/305; A61B 2002/30504; A61B 2002/30505; A61B 2002/30599
USPC ..................... 606/246–279; 623/7.11–17.161
See application file for complete search history.

(56) References Cited

U.S. PATENT DOCUMENTS

| | | | |
|---|---|---|---|
| 2009/0036222 A1 | 2/2009 | Hu | |
| 2009/0138016 A1 | 5/2009 | Berthusen et al. | |
| 2011/0172709 A1 | 7/2011 | Lyons et al. | |
| 2012/0101528 A1* | 4/2012 | Souza | A61B 17/7068 606/249 |
| 2012/0253396 A1* | 10/2012 | Stern | A61B 17/7065 606/249 |
| 2012/0283778 A1 | 11/2012 | Yeh | |
| 2013/0041408 A1 | 2/2013 | Dinville et al. | |
| 2013/0184754 A1* | 7/2013 | Taber | A61B 17/7068 606/249 |
| 2015/0148844 A1* | 5/2015 | Zappacosta | A61B 17/7067 606/248 |

FOREIGN PATENT DOCUMENTS

| | | |
|---|---|---|
| WO | 2009083276 A1 | 7/2009 |
| WO | 2013052496 A2 | 4/2013 |

* cited by examiner

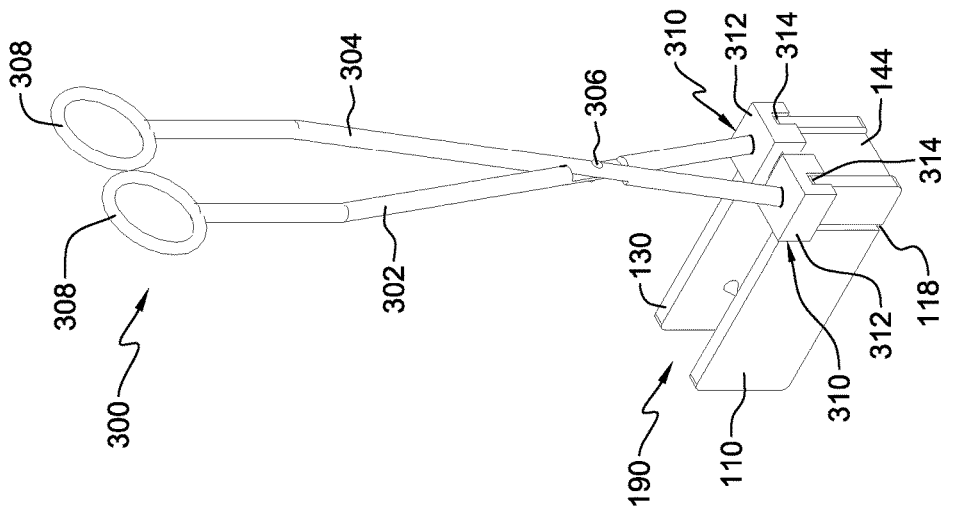
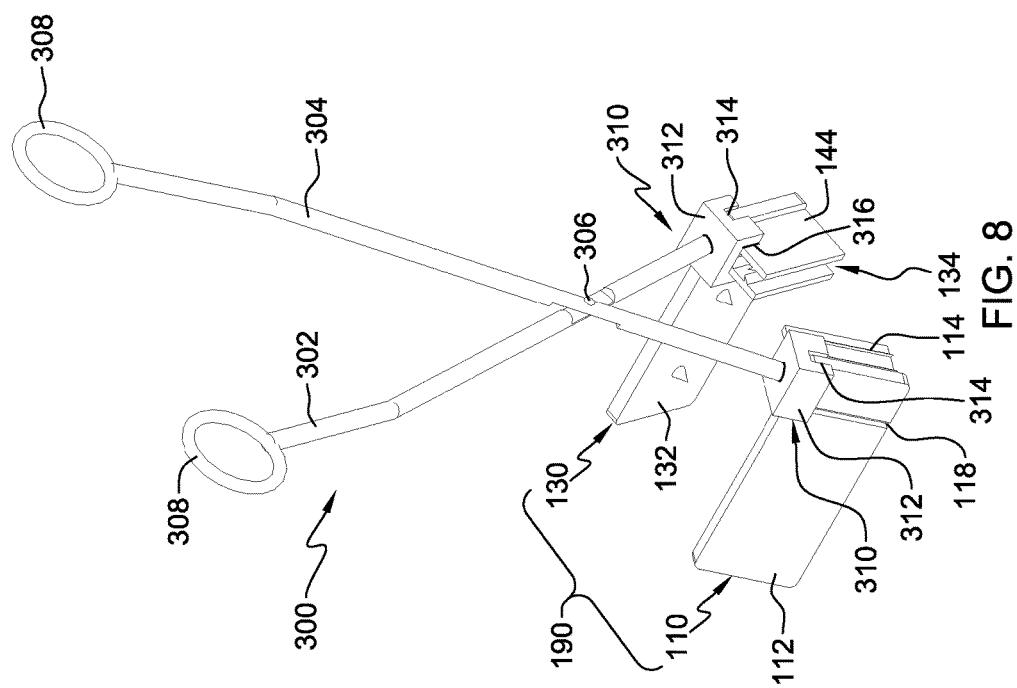

INTERSPINOUS PROCESS FIXATION DEVICES, SYSTEMS, INSTRUMENTS AND METHODS OF ASSEMBLY AND USE

CROSS REFERENCE TO RELATED APPLICATIONS

This application is a continuation of PCT Application No. PCT/US2015/20520 filed on Mar. 13, 2015, which claims priority benefit under 35 U.S.C. § 119(e) of U.S. provisional application No. 61/953,720 filed Mar. 14, 2014, which is incorporated herein by reference in its entirety.

FIELD OF THE INVENTION

The present invention relates generally to general surgery, orthopaedic and neurosurgical implants used for insertion within a patient's spine. More specifically, but not exclusively, the present invention concerns interspinous process fixation devices and systems implanted in the spine for spinal stabilization.

BACKGROUND OF THE INVENTION

Many currently available stabilization devices and methods for the thoracic and lumbar spine require open surgery. During open surgery extensive dissection of the paraspinous musculature and ligamentous attachments from the spinous processes is performed which results in additional risks and recovery time.

Thus, new devices, systems, and methods are needed that reduce or eliminate the extensive dissection of the paraspinous musculature and ligamentous attachments from the spinous processes.

SUMMARY OF THE INVENTION

Aspects of the present invention provide interspinous process fixation devices, systems, instruments, and methods of assembly and use that can maintain or re-establish anatomic spacing of the spinous processes within a patient's spine.

In one aspect, provided herein is a spinous process fixation device, including a first attachment portion and a second attachment portion engaging the first attachment portion, wherein the first attachment portion and the second attachment portion are positioned to couple at least two spinous processes. The first attachment portion including a first member and a second member configured to couple to the first member. The second attachment portion including a third member and a fourth member configured to couple to the third member.

In another aspect, provided herein is a spinous process fixation system, including a spinous process fixation device and an insertion instrument configured for engagement with the spinous process fixation device.

In yet another aspect, provided herein is a method of assembling a spinous process fixation device, including obtaining a first member and a second member. The method may also include coupling the first member to the second member to form a first attachment portion. The method further includes obtaining a third member and a fourth member. In addition, the method includes coupling the third member to the fourth member to form a second attachment portion. Finally, the method includes securing the second attachment portion to the first attachment portion.

In another aspect, provided herein is a method for using a spinous process fixation system including creating an incision in a patient over at least two spinous processes. The method may also include obtaining a first member and a second member of a spinous process fixation device and engaging the first member and the second member with an insertion instrument. The method may further include inserting the insertion instrument with the first member and the second member into the incision and aligning the first member and the second member with a first interspinous process. The method may include actuating the insertion instrument to position the first and second members relative to the first interspinous process and removing the insertion instrument from the patient. Next, the method may include obtaining a third member and a fourth member of the spinous process fixation device and engaging the third member and the fourth member with the insertion instrument. The method may still further include inserting the insertion instrument with the third member and fourth member into the incision and aligning the third member and the fourth member with a second interspinous process. The method may also include actuating the insertion instrument to position the third member and the fourth member relative to a second interspinous process and the third member and the fourth member relative to the first member and the second member. Finally, the method may include removing the insertion instrument and closing the patient.

In a further aspect, provided herein is a spinous process realignment device, including a body, a first pair of moveable members engaged with the body on a first side, and a second pair of moveable members engaged with the body on a second side opposite the first side.

In still a further aspect, provided herein is a method of using a spinous process realignment device, including placing an incision over the patient's spine and obtaining the spinous process realignment device. The method may also include preparing the patient's spine for insertion of the spinous process realignment device and inserting the spinous process realignment device into the patient's spine between two spinous processes. The method may further include aligning the spinous process realignment between the two spinous processes. The method may include inserting an instrument into a first cavity of the interspinous process device and deploying at least one of a first set of moveable members to engage a first spinous process. In addition, the method may also include removing the instrument from the first cavity and inserting the instrument into a second cavity of the interspinous process device. Next, the method may include deploying at least one of a second set of moveable members to engage a second spinous process. Then the method may include removing the instrument from the patient and closing the patient's incision.

In another aspect, provided herein is a reamer instrument, including a first shaft, a second shaft with a reamer portion, and a joint rotatably coupling the first shaft to the second shaft. The joint may include a first body, a second body, and a hinge member for coupling the first body to the second body. The hinge member may include a first pin for rotatably engaging the first body and a second pin for rotatably engaging the second body, wherein the first pin is coupled to the second pin.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which

FIG. 8 is an isometric view of the insertion instrument of FIG. 7 engaging a first attachment portion of the spinous process realignment device of FIG. 1 in an open position, in accordance with an aspect of the present invention;

FIG. 9 is an isometric view of the insertion instrument of FIG. 7 engaging the first attachment portion of the spinous process realignment device of FIG. 1 in a closed position, in accordance with an aspect of the present invention;

DETAILED DESCRIPTION FOR CARRYING OUT THE INVENTION

Figure 1:
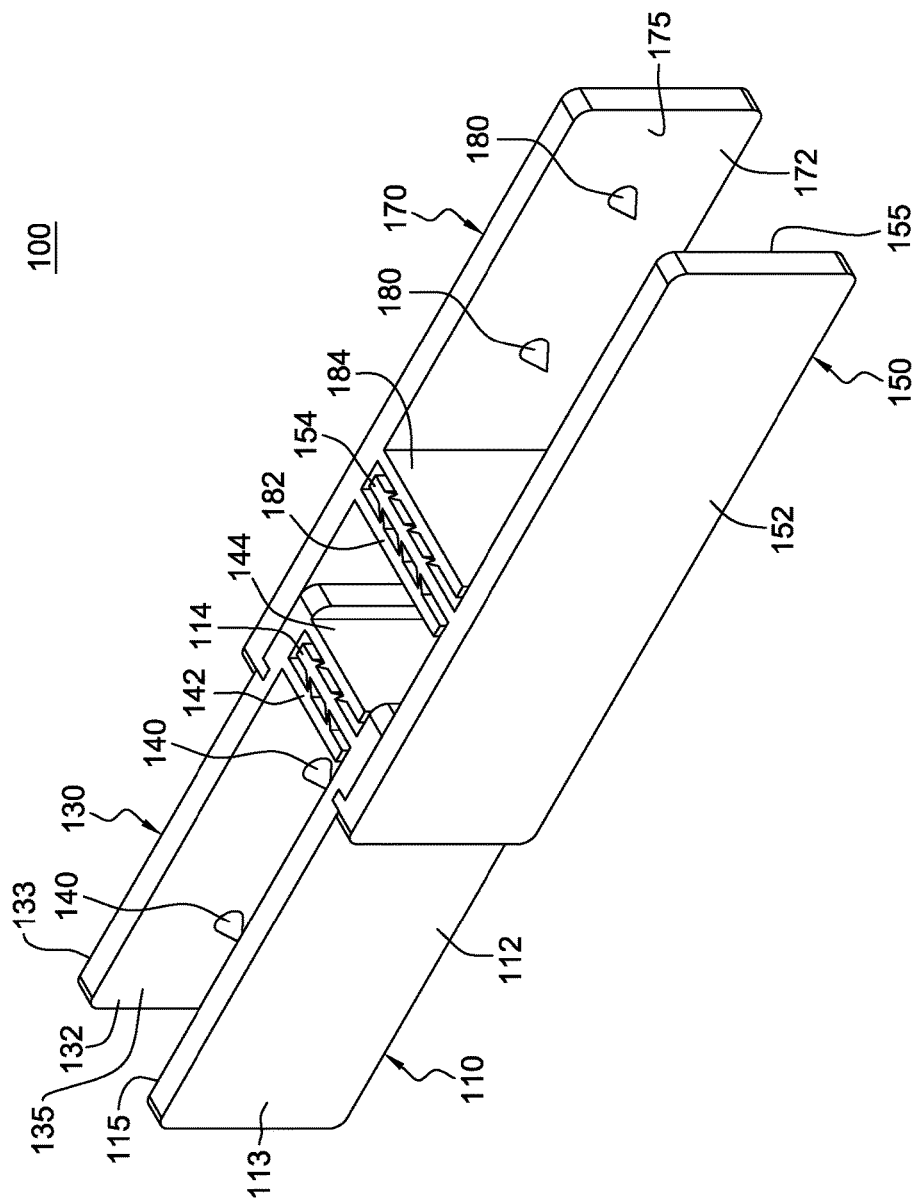
FIG. 1 is a perspective view of an embodiment of a spinous process realignment device, in accordance with an aspect of the present invention.
Figure 2:
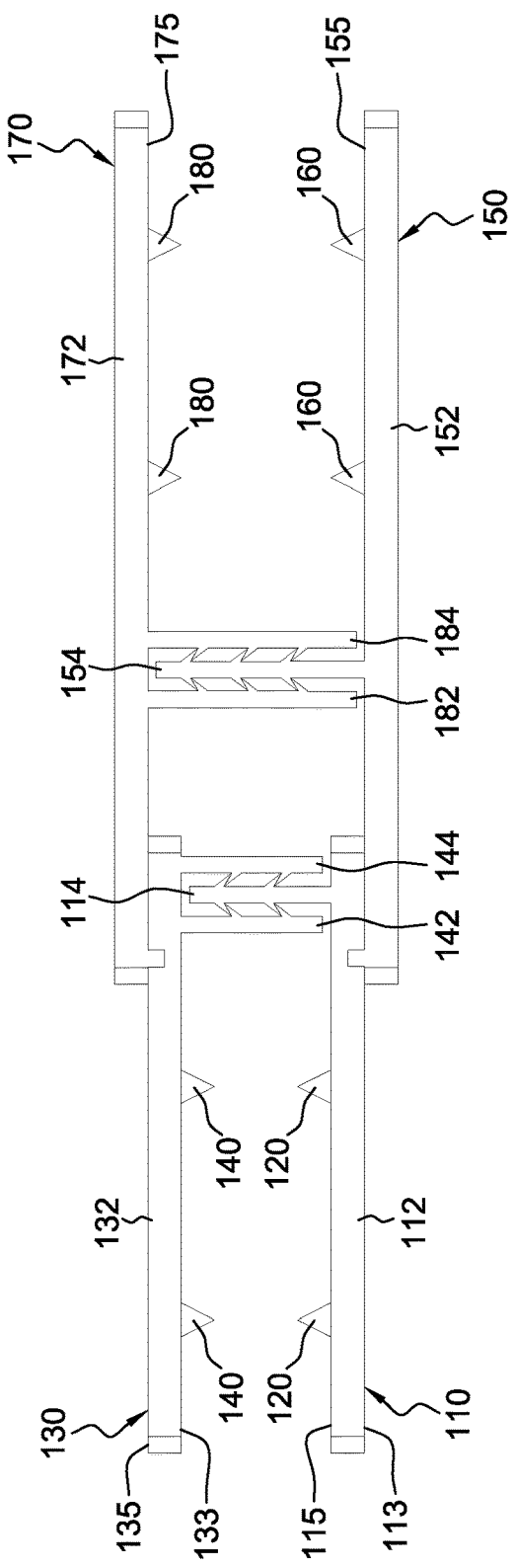
FIG. 2 is a posterior view of the spinous process realignment device of FIG. 1, in accordance with an aspect of the present invention.

Generally stated, disclosed herein are spinous process fixation devices, interspinous process devices, systems, and instruments. Further, methods for assembling and inserting the spinous process fixation devices and interspinous process devices are discussed.

In this detailed description and the following claims, the words proximal, distal, anterior, posterior, medial, lateral, superior, inferior, cephalad and caudally are defined by their standard usage for indicating a particular part of a bone or implant according to the relative disposition of the natural bone or directional terms of reference. For example, "proximal" means the portion of an implant nearest the insertion instrument, while "distal" indicates the portion of the implant farthest from the insertion instrument. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure, "cephalad" means a direction toward the head and "caudally" means a direction toward the inferior part of the body.

Referring to the drawings, wherein like reference numerals are used to indicate like or analogous components throughout the several views, and with particular reference to FIGS. 1-6, there is illustrated an exemplary embodiment of a device 100. The terms "device," "spinous process fixation device," "minimally invasive realignment device," "spinal column realignment device," and "percutaneous interspinous process fixation device" may be used interchangeably herein as they refer to essentially the same device. The device 100 may be configured to restrict painful motion while still allowing for normal motion of the spine by maintaining or stabilizing the spacing and alignment of the spinous processes within a patient's spine. The device 100 may be used, for example, for fusion of the lumbar spine, limited segment fusion of the thoracic spine, posterior stabilization of the anterior lumbar interbody fusion, and for other areas where fusion of the spinous processes is desirable.

Figure 3:
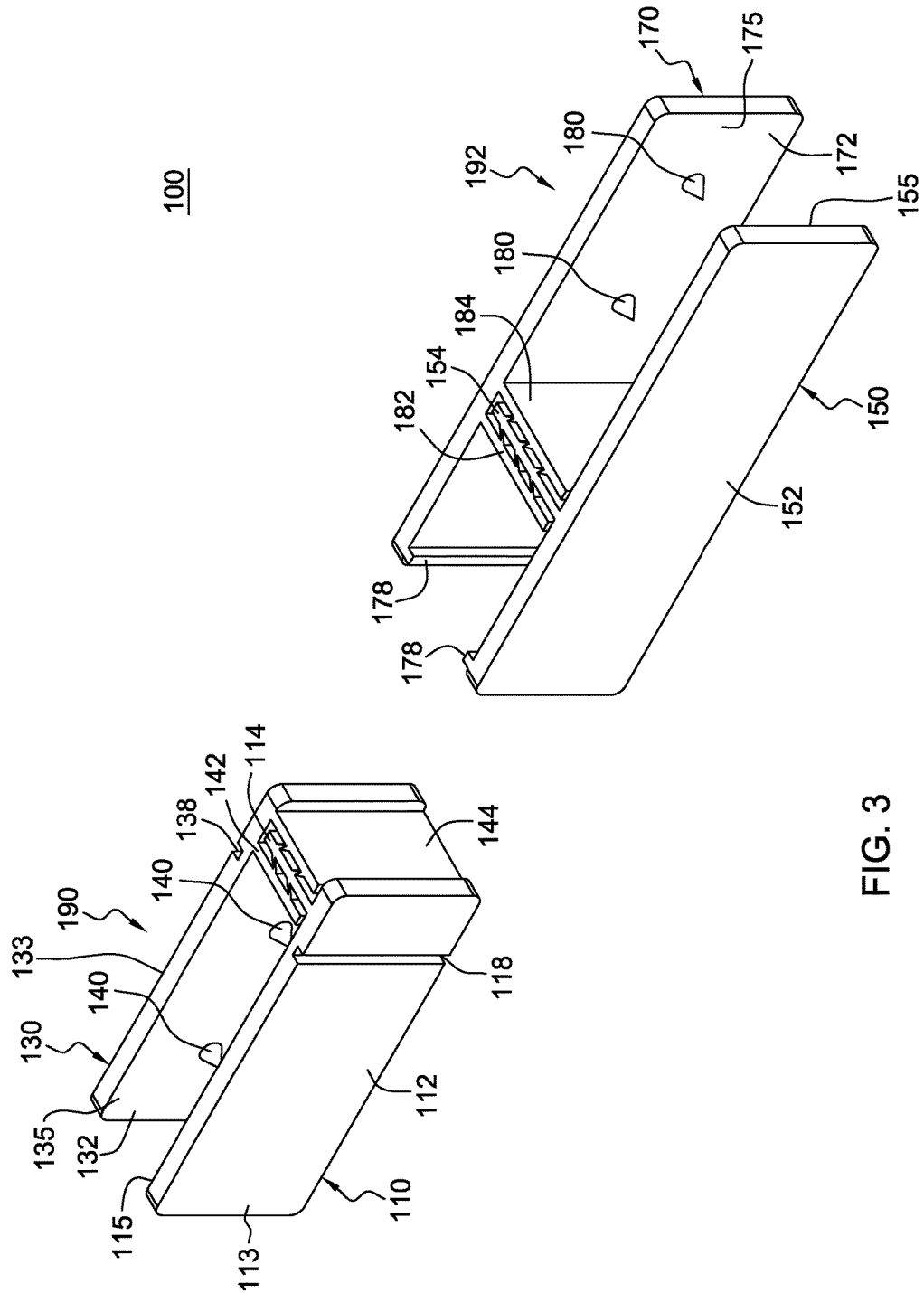
FIG. 3 is a partially exploded perspective view of the spinous process realignment device of FIG. 1, in accordance with an aspect of the present invention.
Figure 4:
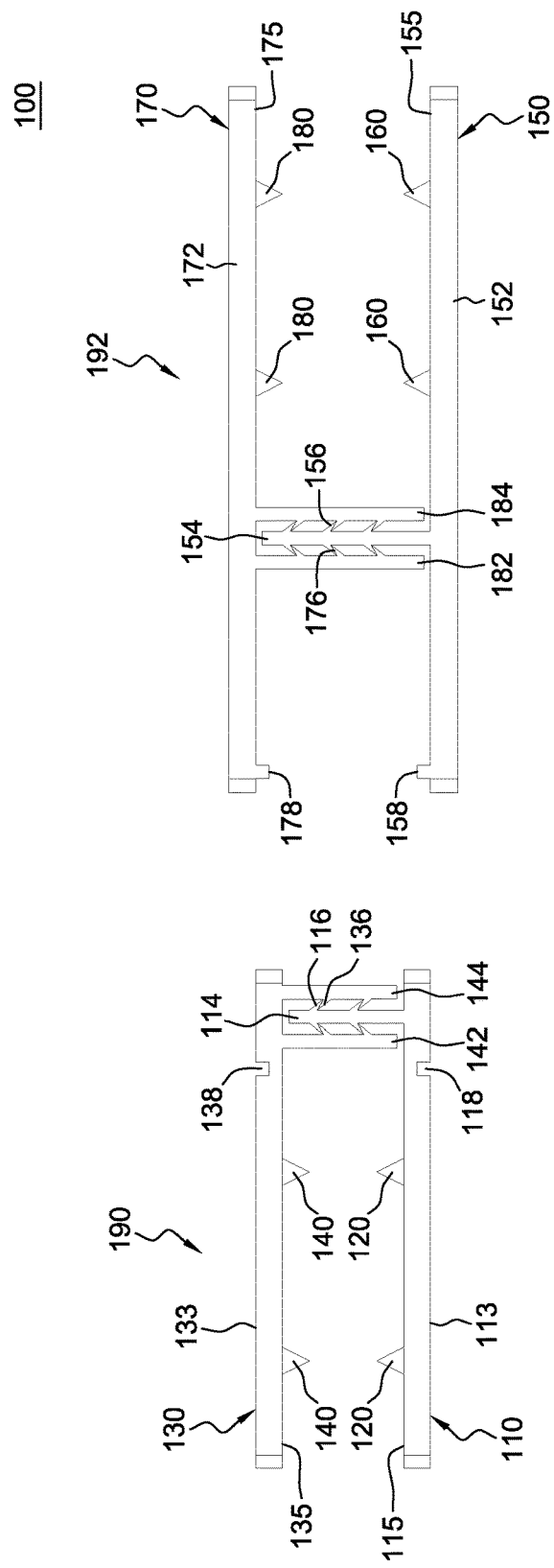
FIG. 4 is a partially exploded posterior view of the spinous process realignment device of FIG. 1, in accordance with an aspect of the present invention.

As shown in FIGS. 1-6, the device 100 may include a first member 110 and a second member 130. Further, the device 100 may include a third member 150 and a fourth member 170. In the depicted embodiment, the first member 110 is configured to engage the second member 130 to form a first attachment portion 190 and the third member 150 is configured to engage the fourth member 170 to form a second attachment portion 192, as shown in FIGS. 3-4.

Figure 5:
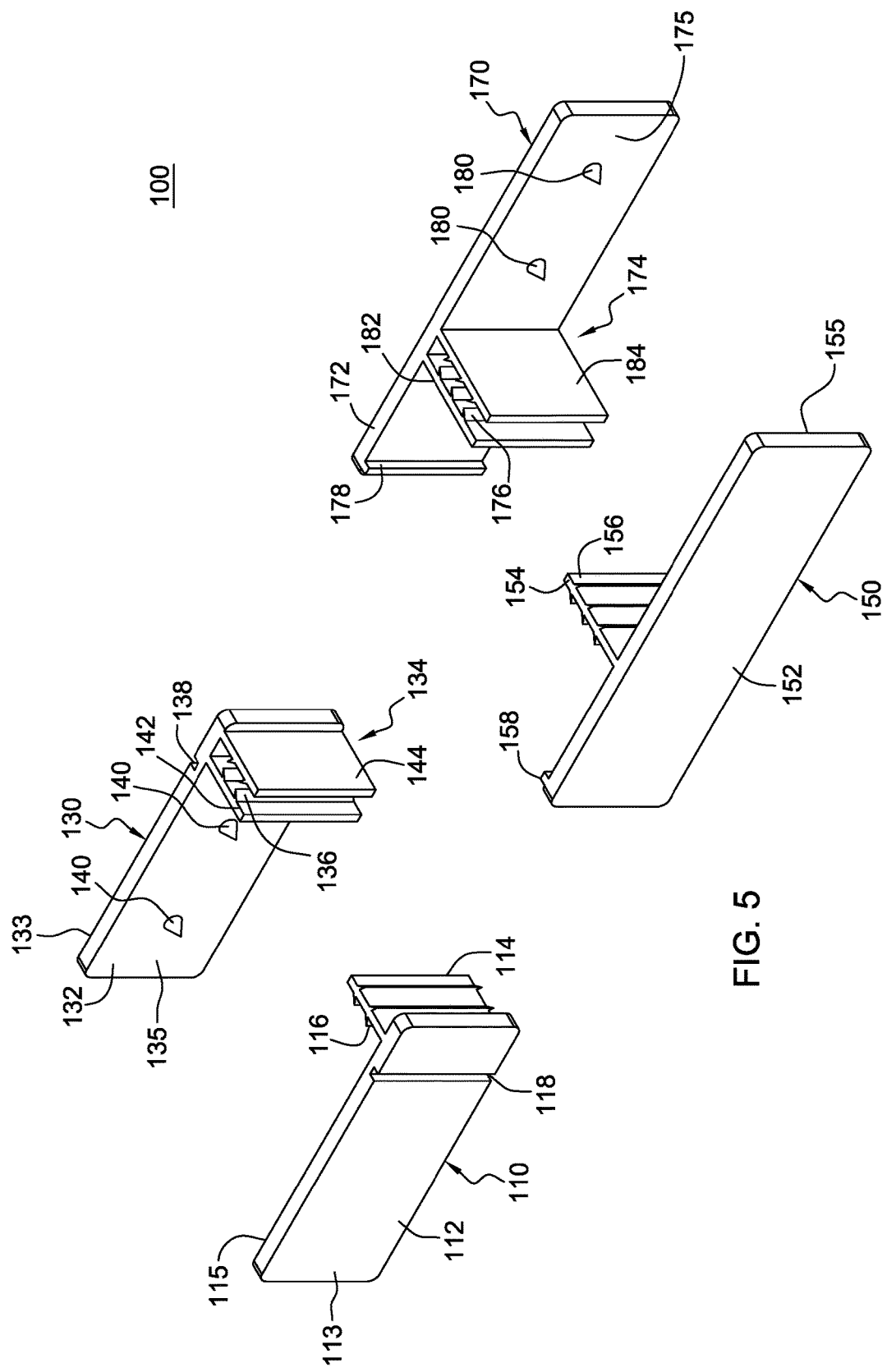
FIG. 5 is an exploded perspective view of the spinous process realignment device of FIG. 1, in accordance with an aspect of the present invention.
Figure 6:
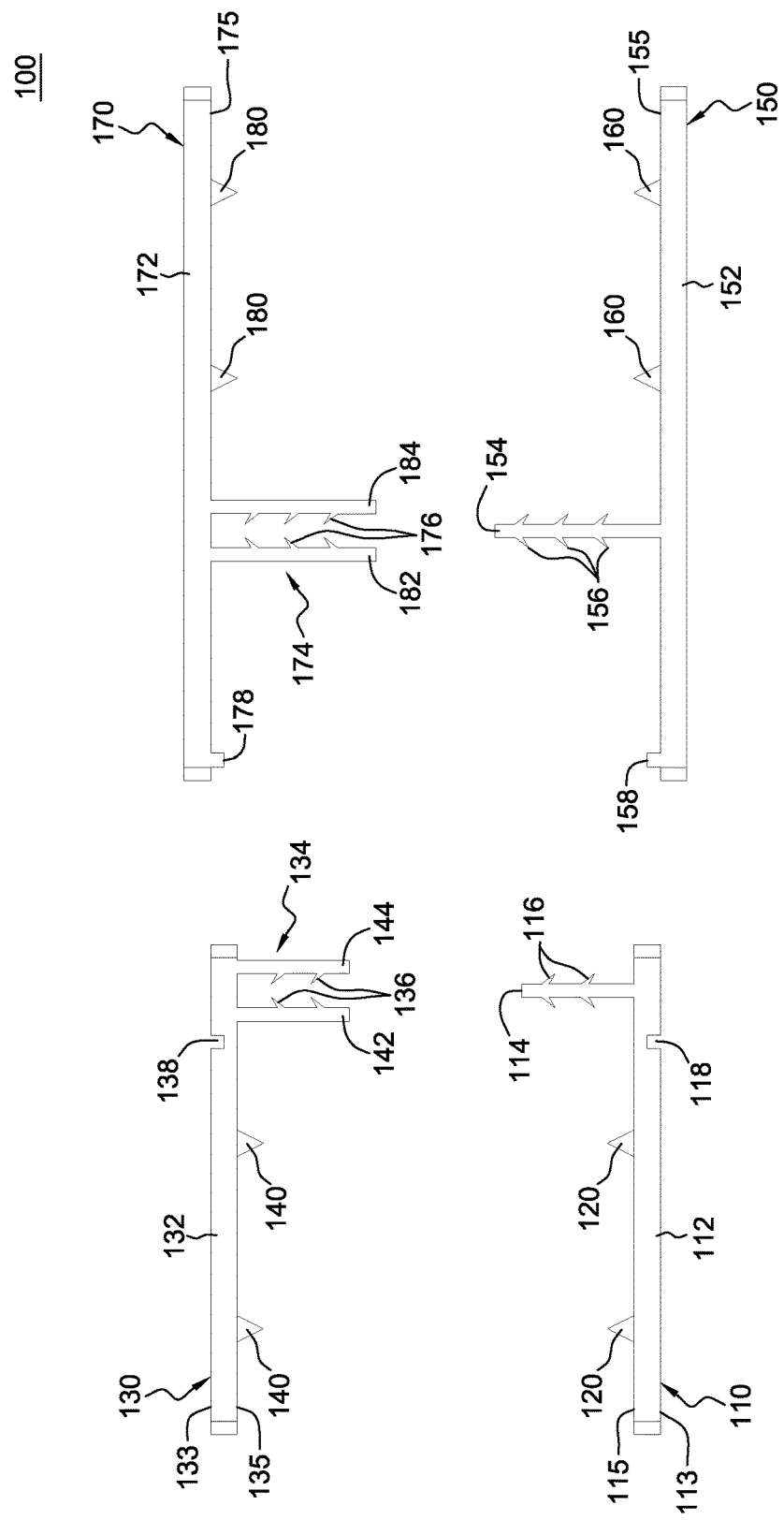
FIG. 6 is an exploded posterior view of the spinous process realignment device of FIG. 1, in accordance with an aspect of the present invention.
Figure 7:
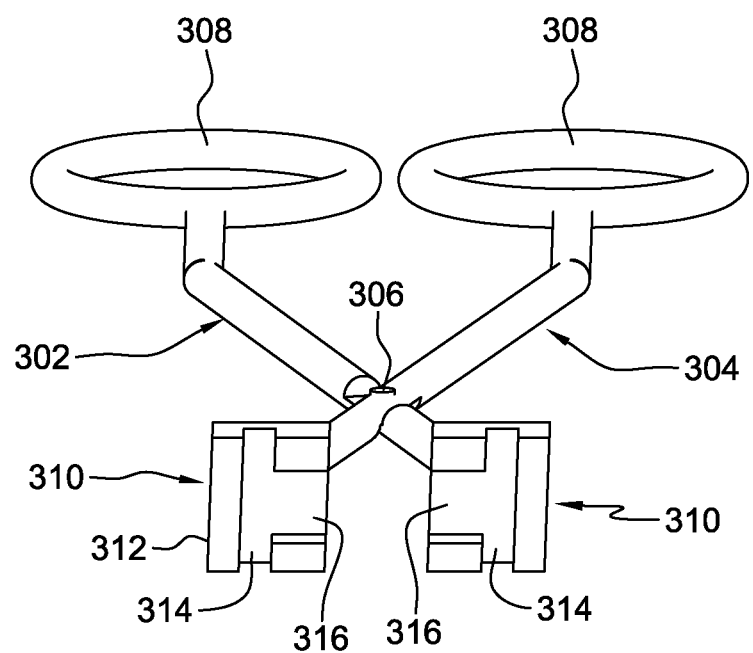
FIG. 7 is a bottom view of an insertion instrument, in accordance with an aspect of the present invention.

As shown in FIGS. 5 and 6, the first member 110 may include a body 112 with an engagement portion or member 114 which may extend out from the body 112, for example, in a relatively perpendicular direction. The engagement portion 114 may include a plurality of teeth 116 on the side surfaces. The body 112 may also include a slot 118 on an exterior surface 113. The slot 118 may extend from a first side to a second side on the exterior surface 113 near, for example, the bottom of the body 112. In addition, the first member 110 may include at least one engagement protrusion 120 on an interior surface 115 of the body 112, as shown in FIG. 6. The at least one engagement protrusion or protuberance 120 may be positioned, for example as shown in the depicted embodiment, above the engagement portion 114 and toward the top of the body 112. The at least one engagement protrusion 120 may include, for example, spikes, ridges, serrations, teeth, and other forms of coatings or textures that produce a rough surface for engaging with a spinous process to secure the first member 110 to the spinous process.

With continued reference to FIGS. 5 and 6, the second member 130 may include a body 132 with an engagement portion or member 134 which may extend away from the body 132, for example, in a generally perpendicular direction. The engagement portion 134 may include a first engagement segment 142 and a second engagement segment 144. The first and second engagement segments 142, 144 may be positioned parallel to each other and perpendicular to the long axis of the body 132 to create a channel sized to receive engagement portion 114. The engagement portion 134 may also include a plurality of teeth 136 positioned on the interior surfaces of the engagement portion 134. The plurality of teeth 136 may be positioned on the inner surface of the first engagement segment 142 and the inner surface of the second engagement segment 144. The plurality of teeth 136 may also be configured to engage the plurality of teeth 116 on the engagement portion 114 of the first member 110.

The body 132 may also include a slot 138 on an exterior surface 133 which extends between the first side and second side of the exterior surface 133 near the bottom of the body 132. The second member 130 may also include at least one engagement protrusion or protuberance 140 on the interior surface 135 of the body 132. The at least one engagement protrusion 140 may be positioned on the interior surface 135 of the body 132, for example, as shown in the depicted embodiments. The at least one engagement protrusion 140 is positioned on one side of the engagement portion 134 and toward the end of the body 132. The at least one engagement protrusion 140 is configured similar to engagement protrusion 120.

Also shown in FIGS. 5 and 6, the third member 150 may include a body 152 with an engagement portion or member 154. The engagement portion 154 may extend away from the body 152, for example, in a relatively perpendicular direction from the interior surface 155. The engagement portion 154 may include a plurality of teeth 156 on the side surfaces. The body 152 may also include a protrusion 158 on an interior surface 155. The protrusion 158 may extend, for example, away from the body 152 in a relatively perpendicular direction and may extend from the first side to the second side of the interior surface 155 near the top of the body 152. The protrusion 158 may be shaped and sized to engage the corresponding slot 118 in the first member 110 or the slot 138 in the second member 130. As shown in FIG. 6, the third member 150 may also include at least one engagement protrusion or protuberance 160 positioned on an interior surface 155 of the body 152. The at least one engagement protrusion 160 may be positioned, for example, on one side of the engagement portion 154 and toward the end of the body 152. The at least one engagement protrusion 160 is configured similar to engagement protrusions 120, 140.

The fourth member 170 may include a body 172 with an engagement portion 174. The engagement portion or member 174 may extend away from the body 172, for example, in a generally perpendicular direction. The engagement portion 174 may also include a first engagement segment 182 and a second engagement segment 184. The first and second engagement segments 182, 184 may be positioned, for example, parallel to each other to create a channel sized to receive engagement portion 154 and perpendicular to the long axis of the body 172. The engagement portion 174 may also include a plurality of teeth 176. The plurality of teeth 176 may be positioned, for example, on the interior surfaces of the engagement portion 174. The plurality of teeth 176 may be positioned on the inner surface of the first engagement segment 182 and the inner surface of the second engagement segment 184. The plurality of teeth 176 may also be configured, for example, to engage with the plurality of teeth 156 on the engagement portion 154 of the third member 150. The body 172 may also include a protrusion 178 that extends away from an interior surface 175 of body 172. The protrusion 178 is oriented in a relatively perpendicular direction and may extend from the first side to the second side of the interior surface 175 near the top of the body 172. The protrusion 178 may be, for example, shaped and sized to engage the slot 118 in the first member 110 or the slot 138 in the third member 130. The fourth member 170 may also include at least one engagement protrusion or protuberance 180 on the interior surface 175 of the body 172. The at least one engagement protrusion 180 may be positioned on the interior surface 175 of the body 172, for example, as shown in FIGS. 5 and 6, the at least one engagement protrusion 180 is positioned below the engagement portion 174 and toward the end of the body 172 and is configured similar to engagement protrusions 120, 140, 160. The at least one engagement protrusion may be, for example, spikes, ridges, serrations, teeth, and other forms of coatings or textures that produce a rough surface for engaging with a spinous process to secure the fourth member 170 to the spinous process.

An insertion instrument or insertion tool 300 is shown in FIGS. 7-9 and 11-12. The insertion instrument 300 may include a first member 302 and a second member 304. The first member 302 and second member 304 may be moveably coupled together at a pivot point 306. In addition, the first member 302 and second member 304 may each include a handle portion 308 at a first end and an engagement portion 310 at a second end. The engagement portions 310 may include a body 312 with a first groove 314 and a second groove 316. The first groove 314 and the second groove 316 may be positioned on the bottom surfaces of the engagement portions 310. The first groove 314 may be positioned, for example, along the longitudinal axis of the engagement portion 310 and the second groove 316 may extend from the medial surface of the engagement portion 310 to engage the first groove 314. The second groove 316 may be, for example, generally perpendicular to the first groove 314.

Figure 10:
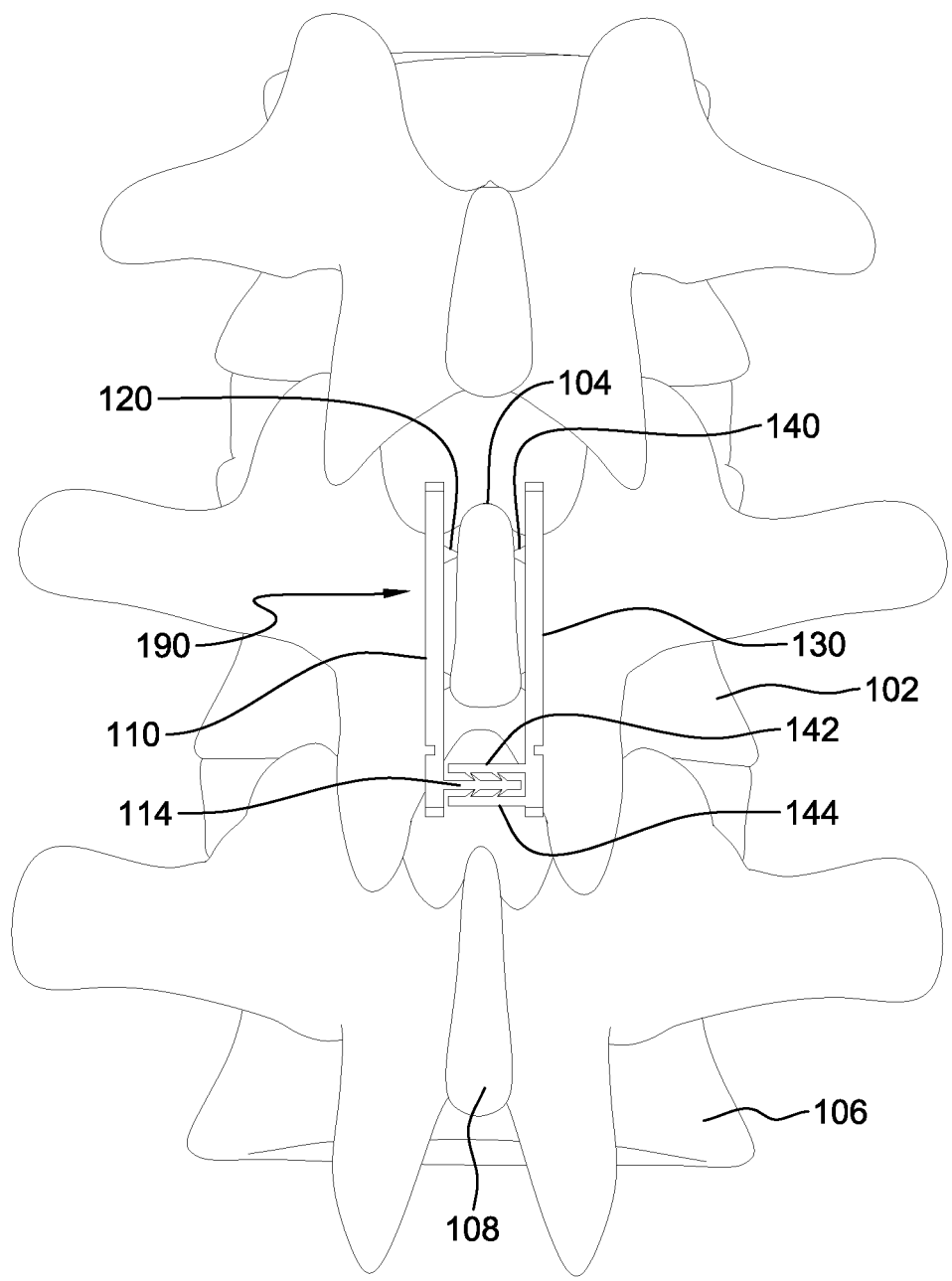
FIG. 10 is a posterior view of the patient's spine showing the first attachment portion of the spinous process realignment device of FIG. 1 implanted on the patient's spine, in accordance with an aspect of the present invention.

As shown in FIGS. 8-9, the insertion instrument 300 may engage the first attachment portion 190 for insertion into a patient. A first engagement portion 310 of the insertion instrument 300 may engage a portion of the body 112 and the engagement portion 114 of the first member 110 and a second engagement portion 310 of the insertion instrument 300 may engage a portion of the body 132 and the engagement portion 134 of the second member 130. The body 310 of the second member 304 of the insertion instrument 300 may engage the first member 110 by, for example, coupling the first groove 314 to a portion of the body 112 and the second groove 316 to a portion of the engagement portion 114 on the first end of the first member 110. The body 310 of the first member 302 of the insertion instrument 300 may engage the second member 130 by, for example, coupling the first groove 314 to a portion of the body 132 and the second groove 316 to a portion of the engagement portion 134 on the first end of the second member 130. The first member 110 and second member 130 may be coupled to the insertion instrument 300 in an open position as shown in FIG. 8 and then once inserted into the patient the first member 110 and second member 130 may be moved to a closed position, as shown in FIG. 9. As shown in FIG. 10 and described in greater detail below with reference to FIG. 15, when the first member 110 and second member 130 are moved to a closed position, they form the first attachment portion 190 and may be coupled to, for example, the spinous process 104 of the patient's first vertebrae 102.

Figure 11:
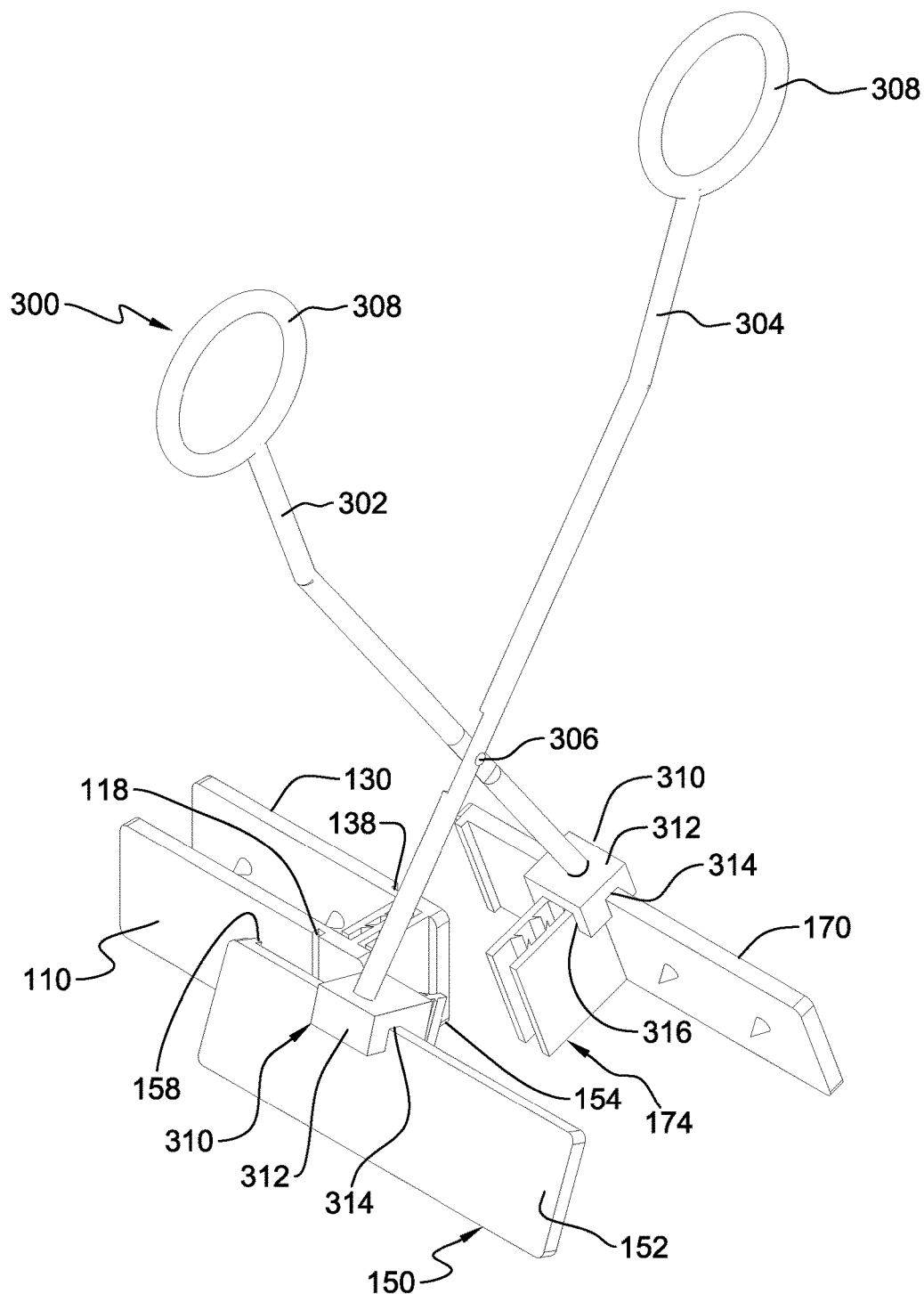
FIG. 11 is an isometric view of the insertion instrument of FIG. 7 engaging the second attachment portion of the spinous process realignment device of FIG. 1 in an open position and the first attachment portion of the spinous process realignment device of FIG. 1 in a closed position, in accordance with an aspect of the present invention.
Figure 12:
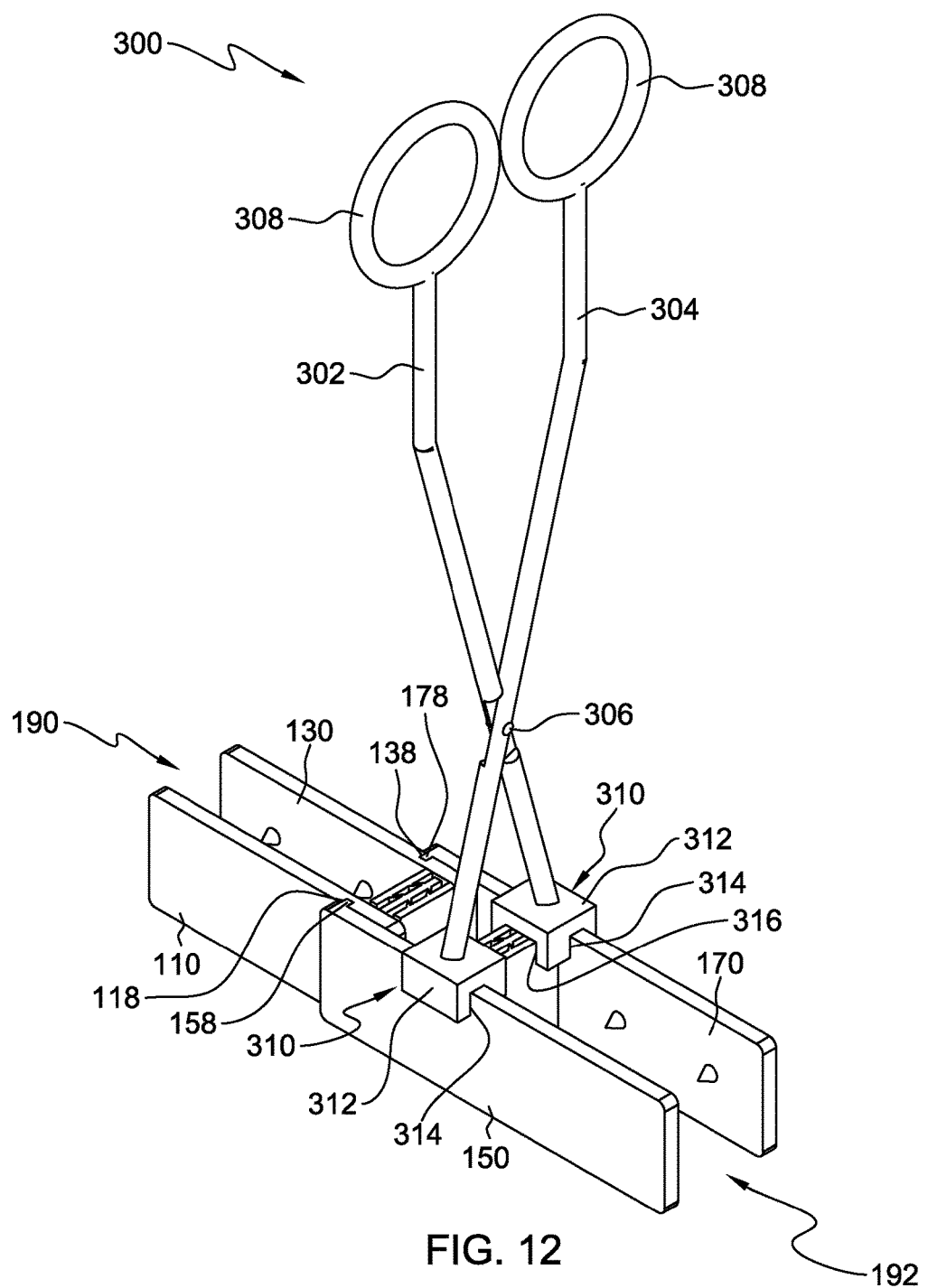
FIG. 12 is an isometric view of the insertion instrument of FIG. 7 engaging the second attachment portion of the spinous process realignment device of FIG. 1 in a closed position engaging the first attachment portion of the minimally invasive realignment device of FIG. 1, in accordance with an aspect of the present invention.
Figure 13:
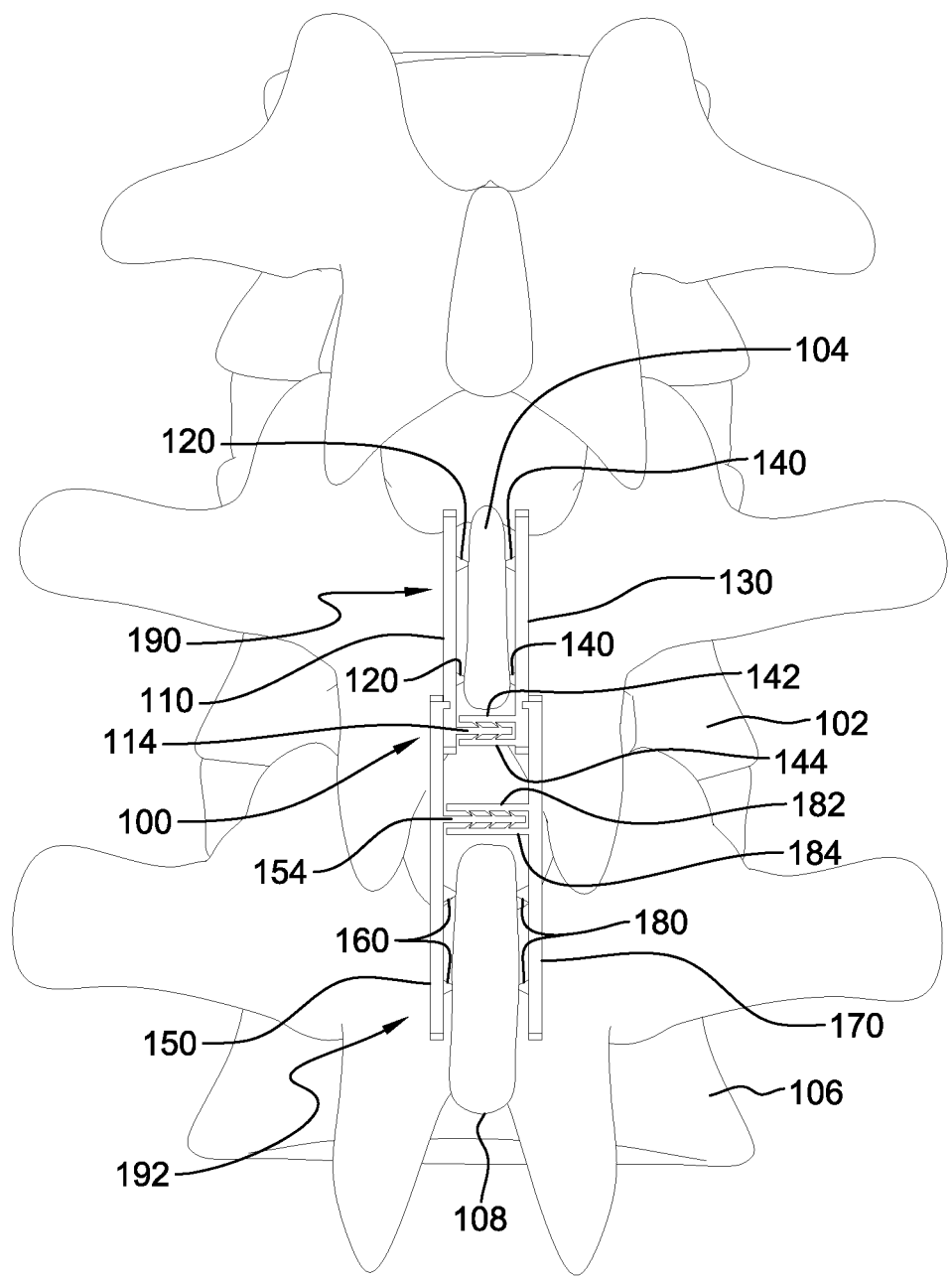
FIG. 13 is a posterior view of the patient's spine showing the first and second attachment portions of the spinous process realignment device of FIG. 1 implanted on the patient's spine, in accordance with an aspect of the present invention.
Figure 14:
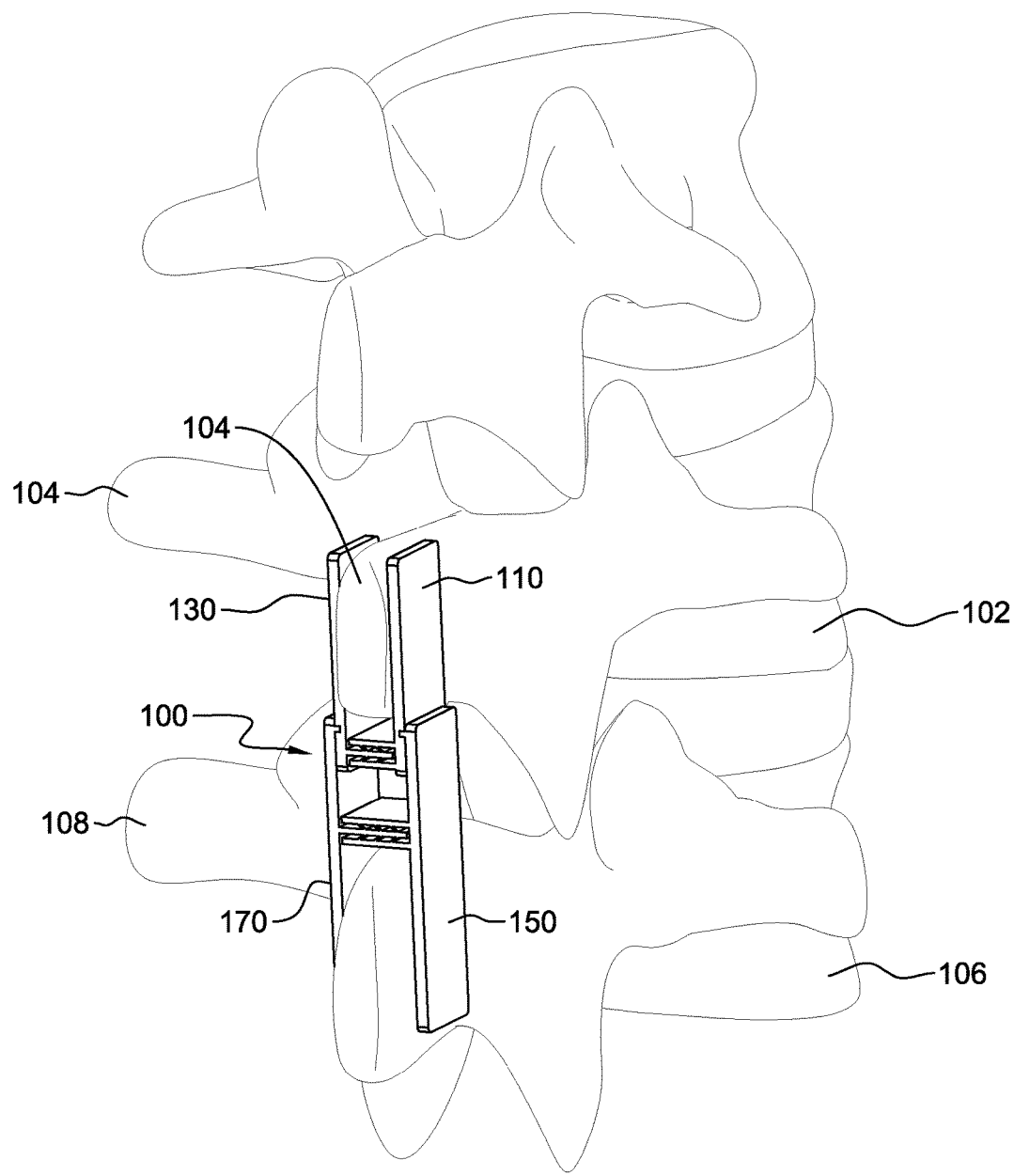
FIG. 14 is a posterior, lateral perspective view of the patient's spine showing the spinous process realignment device of FIG. 1 implanted on the patient's spine, in accordance with an aspect of the present invention.

As shown in FIGS. 11-12 the insertion instrument 300 may also engage the second attachment portion 192 for insertion into a patient and coupling with the first attachment portion 190. The insertion instrument 300 may be coupled to the third member 150 of the second attachment portion 192 by, for example, engaging the first groove 314 of the engagement portion 310 of the second member 304 with the body 152 of the third member 150. In addition, the second groove 316 of the engagement portion 310 of the second member 304 is engaged with the engagement portion 154 of the third member 150. The insertion instrument 300 is also coupled to the fourth member 170 by, for example, engaging the first groove 314 of the engagement portion 310 of the first member 302 with the body 172 of the fourth member 170. In addition, the second groove 316 of the engagement portion 310 of the first member 302 is engaged with the engagement portion 174 of the fourth member 170. As shown in FIG. 11, the third member 150 and fourth member 170 may be coupled to the insertion instrument 300 in, for example, an open position for insertion into the patient. Once inserted into the patient, the third member 150 and fourth member 170 may be moved to a closed position, as shown in FIG. 12. When the third member 150 and fourth member 170 are moved to a closed position, the second attachment portion 192 is formed and secured to the first attachment portion 190 and the spinous process 108 of the patient's second vertebrae 106, as shown in FIGS. 13-14 and described in greater detail below with reference to FIG. 15.

A method for assembling the spinous process fixation device 100 is shown in FIGS. 8-9 and 11-12. The method may include, for instance, obtaining a first member 110 and a second member 130 of the device 100. The method may also include coupling the first member 110 and second member 130 to an instrument 300 and activating the instrument 300 to secure the first member 110 and second member 130 together. The instrument 300 may then be removed from the first member 110 and second member 130. Next, the method may include obtaining a third member 150 and fourth member 170 of the device 100. The third member 150 and fourth member 170 may then be secured to the instrument 300. The method may also include aligning the third and fourth members 150, 170 with the coupled first and second members 110, 130. The instrument 300 may then be activated to secure the third member 150 to the fourth member 170 and to also couple the third and fourth members 150, 170 to the coupled first and second members 110, 130. Once the four members 110, 130, 150, 170 are secured together the instrument 300 may be removed from the third and fourth members 150, 170 leaving assembled device 100.

Figure 15:
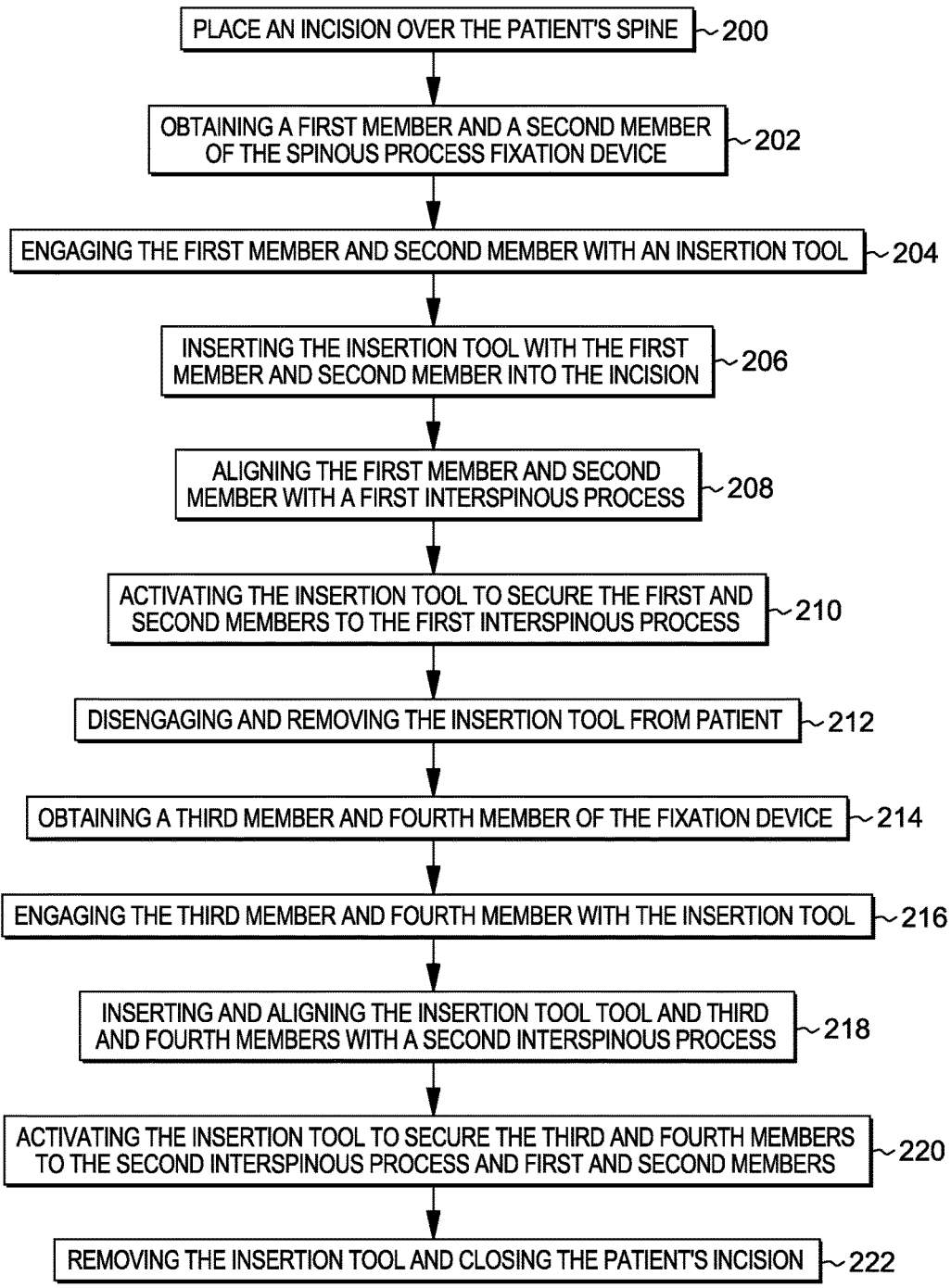
FIG. 15 depicts one embodiment of a method of using a spinous process realignment device, in accordance with an aspect of the present invention.

A method of using the spinous process fixation device 100 in accordance with one or more aspects of the present invention is shown in FIG. 15. The method for using the minimally invasive device 100 may include, for instance: placing an incision over the patient's spine 200; obtaining a first member and second member of the spinous process fixation device 202; engaging the first and second members with an insertion tool 204; inserting the insertion tool with the first and second members through the incision 206; aligning the first and second members with a first interspinous process 208; activating the insertion tool to secure the first and second members to the first interspinous process 210; disengaging the insertion tool from the first and second members and removing the insertion tool from the patient 212; obtaining a third member and a fourth member of the spinous process fixation device 214; engaging the third member and fourth member with the insertion tool 216; inserting and aligning the insertion tool with the attached third and fourth members with the second interspinous process 218; activating the insertion tool to secure the third and fourth members to the second interspinous process and the first and second members 202; and removing the insertion tool and closing the patient's incision 222.

The method of using the spinous process fixation device 100, shown in FIG. 15, may be described in greater detail with reference to FIGS. 8-14 and also includes making an incision over two adjacent spinous processes 104, 108 of two vertebrae 102, 106. A dilator (not shown), such as an expandable dilator, may be inserted into the incision and over the two adjacent aspects of the spinous processes 104, 108. If an expandable dilator is used it may then be expanded to enable access to the spinous processes 104, 108. Alternatively, progressively larger dilators may be inserted over the first dilator to increase the size of the opening and enable access to the spinous processes 104, 108. Once the spinous processes 104, 108 are accessible, they may be prepared for fixation of the device 100. The spinous processes 104, 108 may be prepared by, for example, clearing soft tissue from the spinous processes 104, 108.

The method may further include obtaining a first member 110 and a second member 130 of the device 100 for insertion into a patient. The first member 110 and second member 130 may be secured to an insertion instrument, for example, insertion instrument 300, as shown in FIG. 8 and described in greater detail above. Then, the attached first member 110 and second member 130 may be inserted through the incision into the patient and aligned with the first spinous process 104. The first spinous process 104 may be, for example, the cephalad spinous process, although it is also contemplated that first member 110 and second member 130 may be aligned with and secured to the caudal spinous process. As depicted in FIG. 10, the first member 110 and second member 130 may then be attached to the cephalad spinous process 104 by, for example, activating the insertion instrument 300 to close the first member 110 and second member 130 onto the first spinous process 104 to form a first attachment portion 190. Once the first member 110 and second member 130 have been secured to the first spinous process 104, the insertion instrument 300 may be removed from the patient.

Next, as shown in FIG. 11, the method may include obtaining a third member 150 and fourth member 170 of the device 100 for insertion into the patient. The third member 150 and fourth member 170 may be secured to an insertion instrument, for example, insertion instrument 300 as described in greater detail above with reference to FIG. 11. Then the attached third member 150 and fourth member 170 may be inserted through the incision into the patient and aligned with the second spinous process 108 and the first attachment portion 190. The second spinous process 108 may be, for example, the caudal spinous process, although it is also contemplated that the third member 150 and fourth member 170 may be aligned and attached to the cephalad spinous process. As depicted in FIGS. 13-14, the third member 150 and fourth member 170 may then be attached to the caudal spinous process 108 and may engage the first attachment portion 190 by, for example, activating the insertion instrument 300 to close or engage the third member 150 and fourth member 170 with the second spinous process 108 to form the second attachment portion 192. By activating the insertion instrument 300, the third and fourth members 150, 170 also engage the first attachment portion 190 to complete the assembly of the device 100. The protrusions 158, 178 of the third and fourth members 150, 170, respectively, engage the slots 118, 138 of the first and second members 110, 130, respectively, to secure the first attachment portion 190 to the second attachment portion 192.

In another embodiment of the method of use, it is also contemplated that the first and second members 110, 130 may be positioned with respect to the first spinous process 104 with the insertion instrument 300 removed prior to securing the first and second members 110, 130 to the first spinous process 104. Next, the third and fourth members 150, 170 may be inserted with the insertion instrument 300 and aligned with respect to the second spinous process 108 and the first and second members 110, 130. Once proper alignment of the third and fourth members 150, 170 is achieved, the insertion instrument 300 may be activated to move the third and fourth members 150, 170 to engage the first and second members 110, 130. Once the members 110, 130, 150, 170 are all engaged together, the surgeon may then confirm proper alignment with the spinous processes 104, 108 and then simultaneously secure both the first and second members 110, 130 and the third and fourth members 150, 170 to the first and second spinous processes 104, 108, respectively. In addition, as the insertion instrument 300 is activated the third and fourth members 150, 170 engage the first and second members 110, 130 to assemble the device 100.

When the first and second attachment portions 190, 192 are secured to the spinous processes 104, 108, the insertion instrument 300 may be disengaged from the third and fourth members 150, 170 and removed from the patient's incision. As shown in FIGS. 13-14, the device 100 is secured to the spinous processes 104, 108 and the insertion instrument 300 has been removed, so the patient's incision may now be closed.

Figure 16:
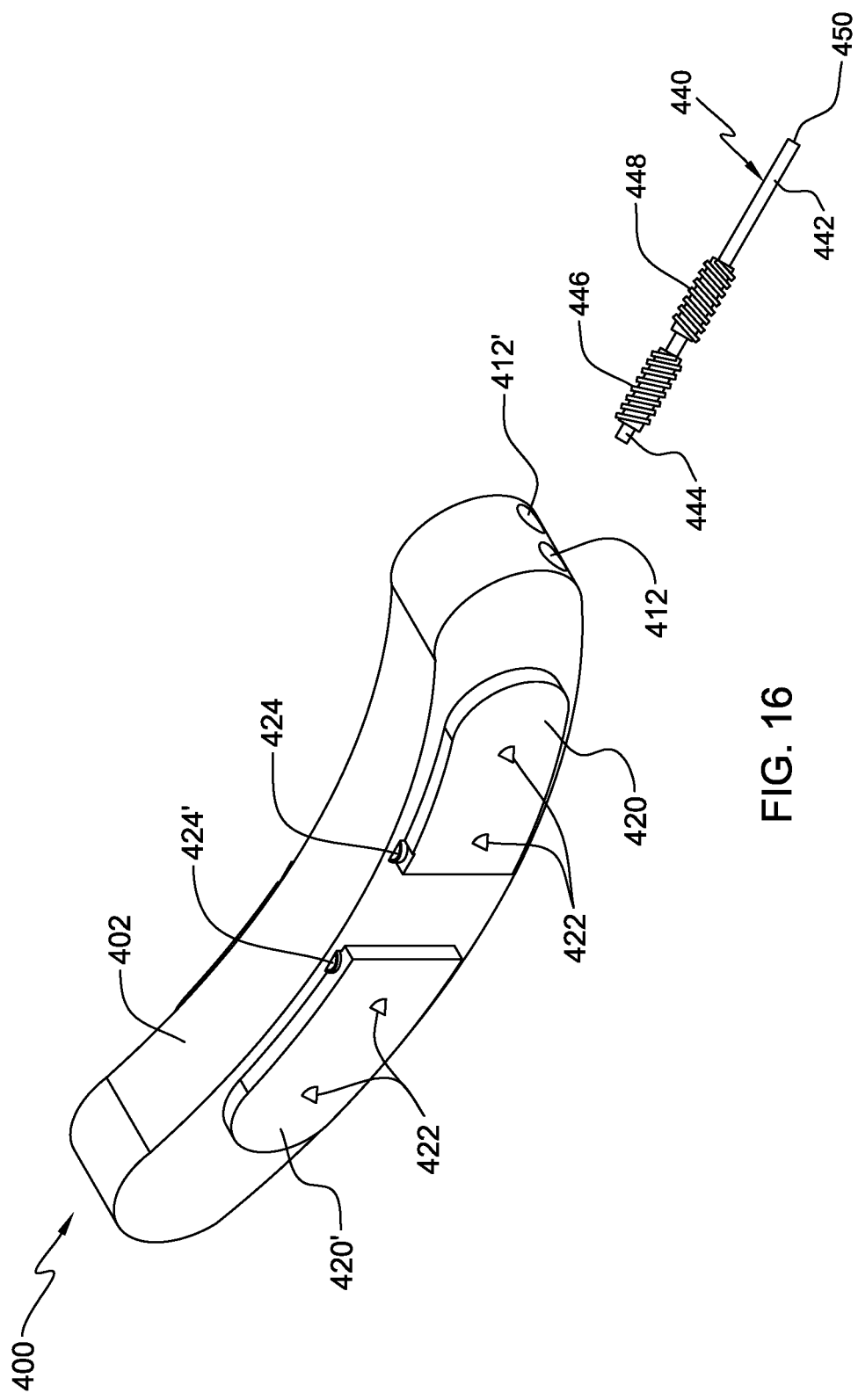
FIG. 16 is a partially exploded perspective view of another embodiment of an interspinous process device, in accordance with an aspect of the present invention.
Figure 17:
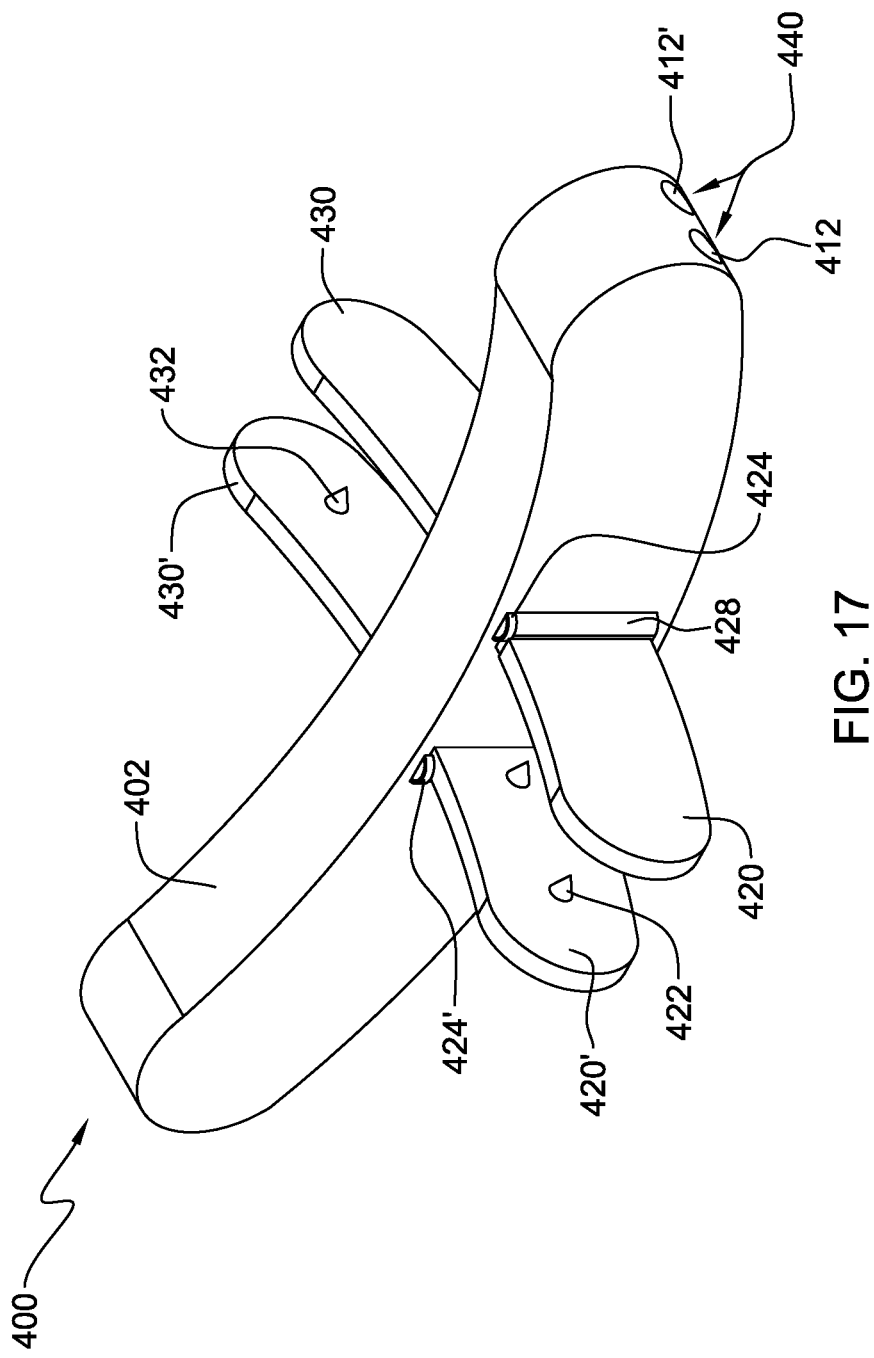
FIG. 17 is a perspective view of the interspinous process device of FIG. 16 with the moveable members deployed, in accordance with an aspect of the present invention.
Figure 18:
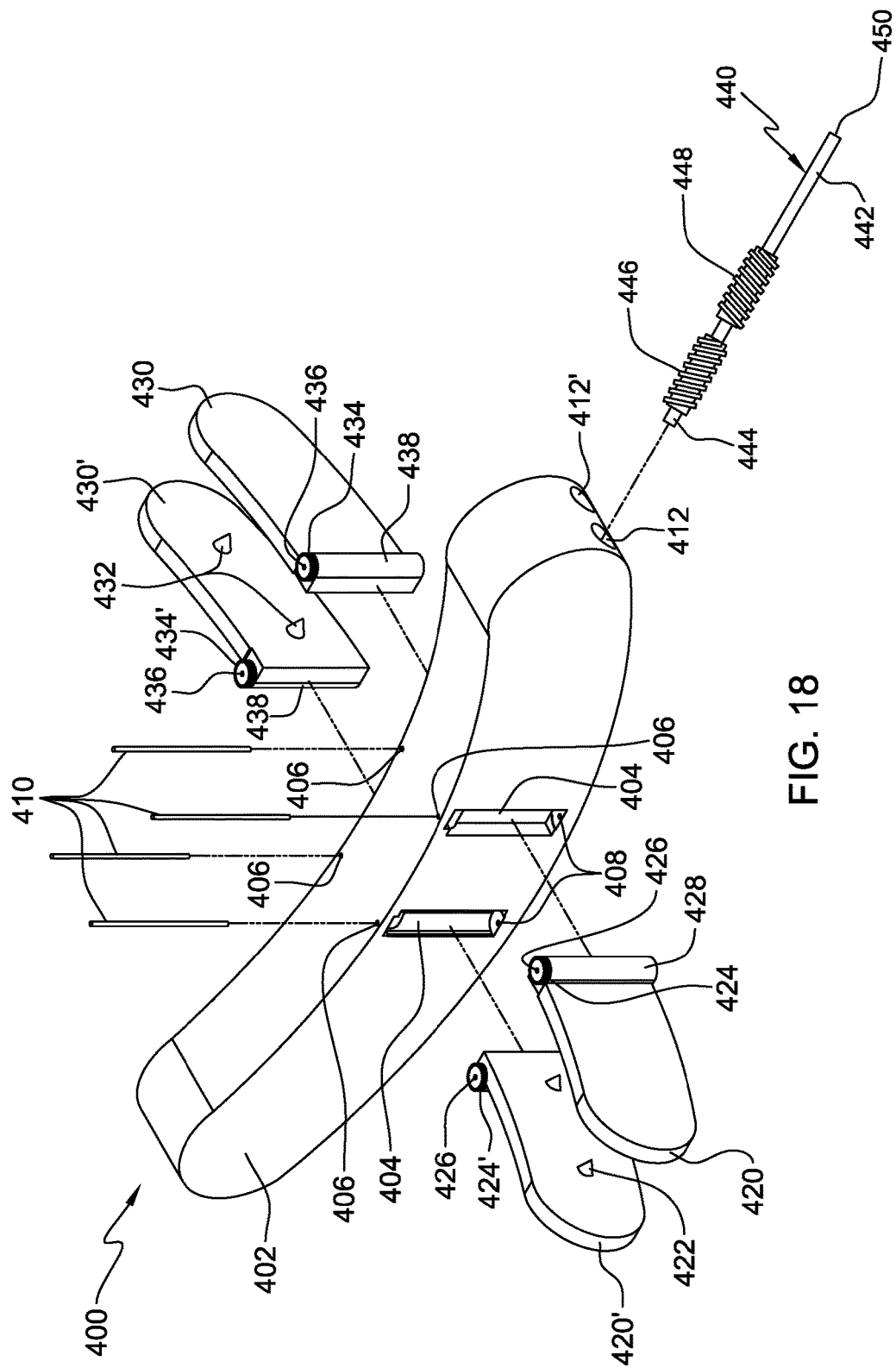
FIG. 18 is an exploded perspective view of the interspinous process device of FIG. 16, in accordance with an aspect of the present invention.

An alternative embodiment of an interspinous process device 400 is shown in FIGS. 16-19. The device 400 may include a body 402 with a first pair of moveable members 420, 420' and a second pair of moveable members 430, 430'. The body 402 may be, for example, curved along the longitudinal axis, such that the body 402 curves in an anterior direction from a central portion toward each end. The curve of the body 402 may be, for example, designed to mimic the shape of the patient's spine. As shown in FIG. 18, the body 402 may include, for example, a plurality of slots 404, a plurality of first openings 406 engaging the slots 404, and a plurality of second openings 408 opposite the first openings 406 and also engaging the slots 404. The plurality of slots 404 may include, for example, a first set of slots 404 on a first side of the body and a second set of slots 404 on a second side of the body opposite the first side. The body 402 may also include at least two cavities 412, 412' extending into the body 402 and engaging at least a portion of the plurality of slots 404. The plurality of slots 404 may be positioned, for example, near the center of the body 402 on the superior and inferior surfaces of the body 402. The device 400 may also include a plurality of pins 410 which may be, for example, sized to pass through the first openings 406, pass through the slots 404, and fit into the second openings 408.

Figure 19:
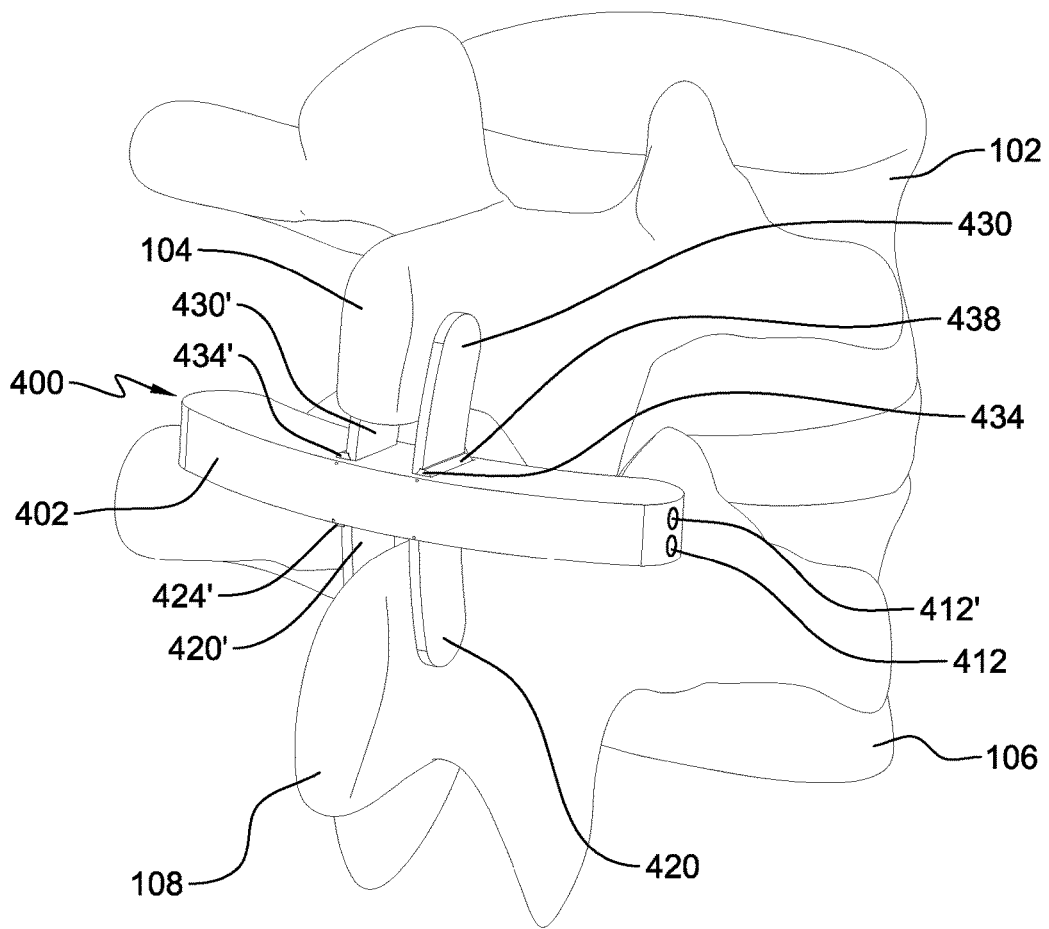
FIG. 19 is a posterior, lateral perspective view of a patient's spine showing the interspinous process device of FIG. 16 implanted in the patient's spine, in accordance with an aspect of the present invention.
Figure 20:
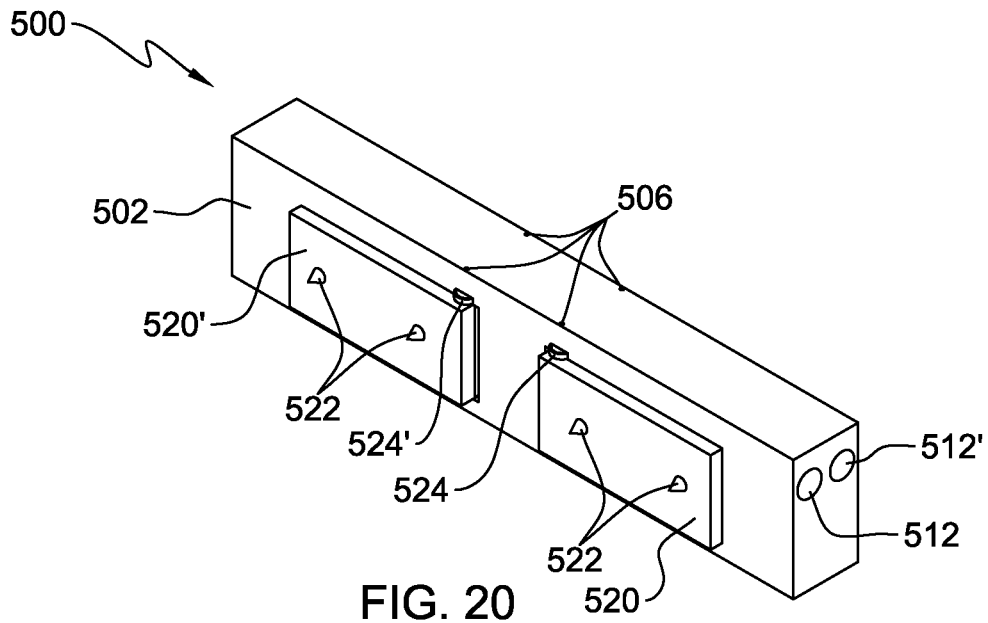
FIG. 20 is a perspective view of yet another embodiment of an interspinous process device, in accordance with an aspect of the present invention.

As shown in FIGS. 16-19, the first pair of moveable members 420, 420' may each include at least one engagement mechanism 422 on the surface of the moveable members 420, 420' that engages a spinous process 108. The at least one engagement mechanism 422 may be, for example, spikes, ridges, serrations, teeth, and other forms of coatings or textures that produce a rough surface for engaging with the spinous process 108 to secure the moveable members 420, 420' to the spinous process 108. The first pair of moveable members 420, 420' may also include a coupling mechanism with a boss 428, a pin 410, and the slots 404. The boss 428 is on a first end of the moveable members 420, 420' shaped to be received within the slots 404. The first pair of moveable members 420, 420' may also include an opening 426 through the boss 428 that is shaped to receive the pin 410. The pin 410 may allow for pivoting movement of the coupling mechanism to allow for the moveable members 420, 420' to pivot relative to the body 402. The securement mechanism is shown as a pin 410 in FIGS. 16-19, but it may also include, for example, a set of detents, a knob, or any other mechanism allowing for pivoting of the moveable members 420, 420'. The boss 428 of the coupling mechanism may be shaped to allow for pivoting movement, for example, the boss 428 may be curved or cylindrical like. The moveable members 420, 420' may also each include a movement mechanism 424, 424' positioned on a top or bottom surface of the bosses 428. Alternatively, the movement mechanism 424, 424' may be positioned intermediate the bosses 428 between the first end and the second end of the bosses 428. The movement mechanism 424, 424' may include, for example, teeth, grooves, or gears (not shown) configured to engage an instrument 440 and corresponding worm gears 446, 448, described in greater detail below, to deploy the moveable members 420, 420'. When the moveable members 420, 420' are deployed they may engage a spinous process 108, as shown in FIG. 19.

The second pair of moveable members 430, 430', as shown in FIGS. 17-19, may each include at least one engagement mechanism 432 on the surface of the moveable members 430, 430' that engages a spinous process 104. The at least one engagement mechanism 432 is configured similar to engagement mechanism 422 for engaging with the spinous process 104 to secure the moveable members 430, 430' to the spinous process 104. The second pair of moveable members 430, 430' may also include a boss 438 on a first end of the moveable members 430, 430' shaped to be received within the slots 404. The second pair of moveable members 430, 430' may also include an opening 436, a pin 410, and a movement mechanism 434 as described above with reference to moveable members 420, 420'. The moveable members 430, 430' may be deployed to engage spinous process 104, as shown in FIG. 19.

Figure 24:
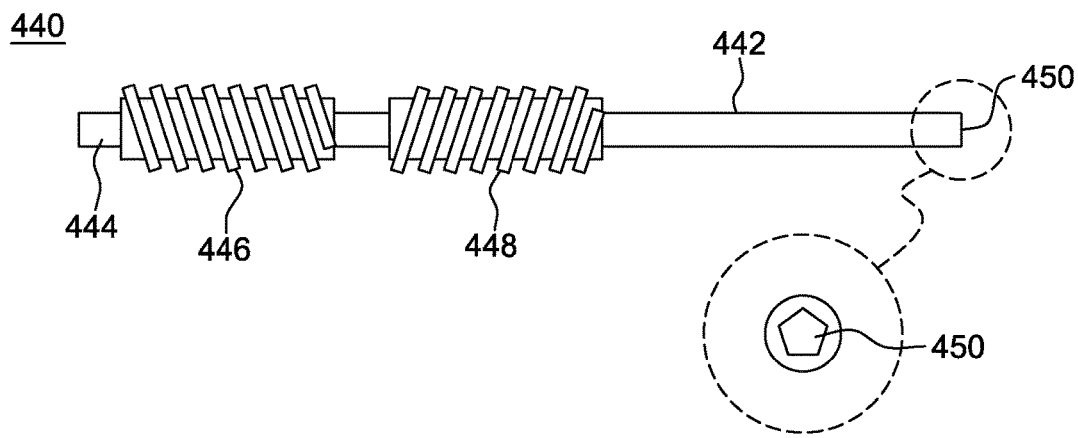
FIG. 24 is a side view of a worm gear mechanism of the interspinous process devices of FIGS. 16 and 20, in accordance with an aspect of the present invention.

As shown in FIGS. 16 and 18, the device 400 may also include at least one worm gear mechanism 440 which may be positioned in the cavities 412, 412'. The at least one worm gear mechanism 440 may be permanently integrated inside the cavities 412, 412' or alternatively, the at least one worm gear mechanism 440 may be removable from the cavities 412, 412'. In one embodiment, a worm gear mechanism 440 is moveably secured in each of the cavities 412, 412'. The worm gear mechanism 440 may include a shaft 442 with a coupling tip 444 for rotatably coupling to the body 402 inside one of the cavities 412, 412', a first worm gear 446, and a second worm gear 448. The first worm gear 446 may be, for example, a right hand worm gear, and the second worm gear 448 may be, for example, a left hand worm gear. Although alternative arrangements for the first and second worm gears 446, 448 are also contemplated including, but not limited to, gear 446 being a left hand gear and gear 448 being a right hand gear, both gears 446, 448 being left hand gears, or both gears 446, 448 being right hand gears. The worm gear mechanism 440 may also have an engagement opening 450 in the shaft 442 on the end opposite the coupling tip 444. The opening 450 may receive a tool, for example, a screwdriver or drill, to rotate the worm gear mechanism 440. The opening 450 may be, for example, a hex opening as shown in FIG. 24, although alternative shapes for the opening 450 are also contemplated.

When inserted into a cavity 412, the coupling tip 444 may sit in a corresponding opening (not shown) positioned past the slot 404 that engages the moveable member 420'. This enables the first worm gear 446 to align and couple with the movement mechanism 424' and the second worm gear 448 to align and couple with the movement mechanism 424 to allow for rotation of the worm gear mechanism 440 to in turn rotate the movement mechanisms 424', 424 to deploy or retract the moveable members 420, 420', as described in greater detail below. When the worm gear mechanism 440 is inserted into cavity 412', the first and second worm gears 446, 448 will align and couple with the movement mechanisms 434', 434, respectively, as described above with reference to cavity 412, which will not be discussed here for brevity sake. Although the adjustment mechanism is shown as a worm gear mechanism 440 in the depicted embodiments, it may also include a spiral thread, rack and pinion, or other alternative mechanism that align with the movement mechanisms 424', 424, 434', 434 to deploy or retract the moveable members 420', 420, 430', 430.

Figure 25:
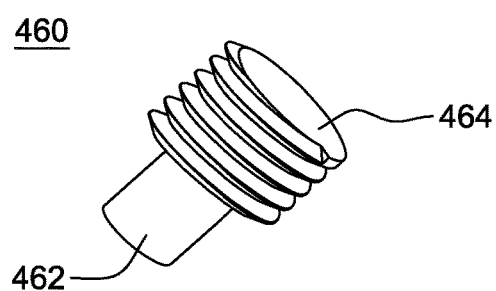
FIG. 25 is a perspective view of a locking mechanism for engagement with the worm gear mechanism of FIG. 24, in accordance with an aspect of the present invention.

The worm gear mechanism 440 may be inset within the cavities 412, 412' to allow for insertion of a locking mechanism 460, as seen in FIG. 25, into each of the cavities 412, 412'. The worm gear mechanism 440 may be inset to allow for the locking mechanism 460 to be inserted flush with the body 402 of the device 400. The locking mechanism 460 may include a stem portion 462 and a head portion 464. The stem portion 462 may be sized to engage the opening 450 of the worm gear mechanism 440. The stem portion 462 may be, for example, slightly smaller than the opening 450 to allow the stem portion 462 to bottom out and prevent the worm gear mechanism 440 from moving after insertion of the locking mechanism 460. The head portion 464 may be sized to engage the cavities 412, 412' of the device 400. To secure the locking mechanism 460 in the body 402, the head portion 464 may be, for example, threaded to engage corresponding threads in the cavities 412, 412'. Alternatively, the head portion 464 may have another means for securing the locking mechanism 460 to the body 402, as known by one of skill in the art, for example, at least one protrusion on the surface of the head portion 464 to engage a lip (not shown) in the opening of the cavities 412, 412'.

In another embodiment of the interspinous process device 400, the at least two cavities may be positioned on opposite ends of the body 402. A first cavity (not shown) may be positioned on a first end and engage at least a portion of two of the slots 404, for example, the slots 404 that receive the moveable members 420, 430. The second cavity (not shown) may be positioned on a second end and engage at least a portion of two of the slots 404, for example, the slots 404 that receive the moveable members 420', 430'. An alternative embodiment of the at least one worm gear mechanism 440 may be inserted into the first cavity to engage the movement mechanisms 424, 434 of the moveable members 420, 430. As the worm gear mechanism 440 is rotated, the worm gear mechanism 440 engages the movement mechanisms 424, 434 to deploy the moveable members 420, 430. The movement mechanisms 424, 434 may be positioned on the bosses 428, 438 to allow for the moveable members 420, 430 to be deployed simultaneously as the worm gear mechanism 440 is rotated within the first cavity. The worm gear mechanism 440 may be inserted into the second cavity to engage the movement mechanisms 424', 434' of the moveable members 420', 430'. As the worm gear mechanism 440 is rotated, the worm gear mechanism 440 engages the movement mechanisms 424', 434' to deploy the moveable members 420', 430'. The movement mechanisms 424', 434' may be positioned on the bosses 428, 438 to allow for the moveable members 420', 430' to be deployed simultaneously as the worm gear mechanism 440 is rotated within the second cavity.

In yet another embodiment of the interspinous process device 400, the body 402 may include one cavity positioned on a first end and extending along the longitudinal axis of the body 402, engaging at least a portion of each slot 404. Another alternative embodiment of the worm gear mechanism 440 may be inserted into the cavity to engage the movement mechanisms 424, 434 of the moveable members 420, 430. The worm gear mechanism 440 may then be rotated, engaging and rotating the movement mechanisms 424, 434 to deploy the moveable members 420, 430. The worm gear mechanism 440 may then be moved to engage the movement mechanisms 424', 434' of the moveable members 420', 430'. The worm gear mechanism 440 may then be rotated, engaging and rotating the movement mechanisms 424', 434' to deploy the moveable members 420', 430'. The movement mechanisms 424, 434 may be positioned on the bosses 428, 438 to allow for the moveable members 420, 430 to be deployed simultaneously as the worm gear mechanism 440 is rotated within the cavity. The movement mechanisms 424', 434' may be positioned on the bosses 428, 438 to allow for the moveable members 420', 430' to be deployed simultaneously as the worm gear mechanism 440 is rotated within the cavity.

Figure 21:
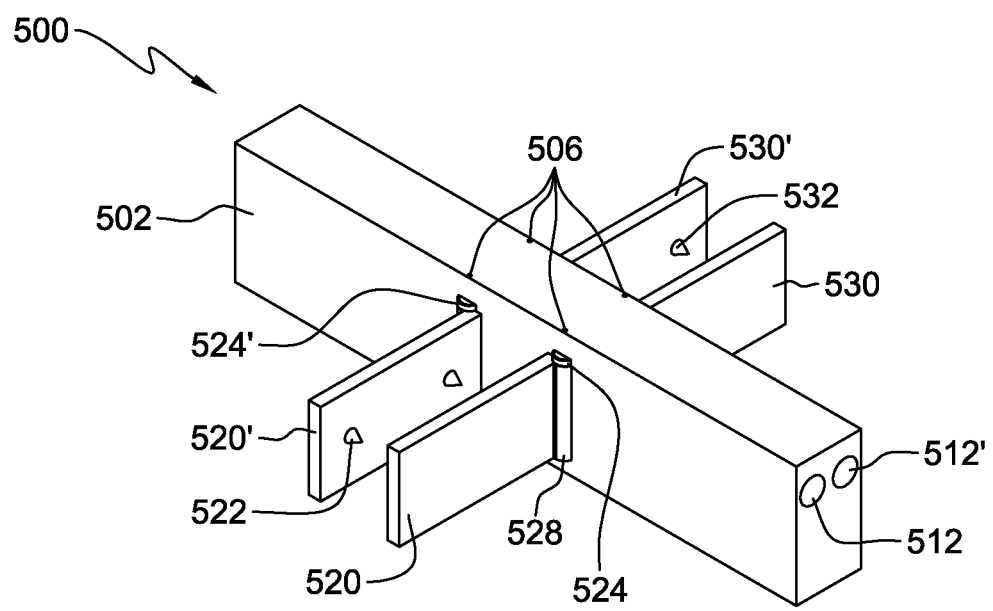
FIG. 21 is a perspective view of the interspinous process device of FIG. 20 with the moveable members deployed, in accordance with an aspect of the present invention.
Figure 22:
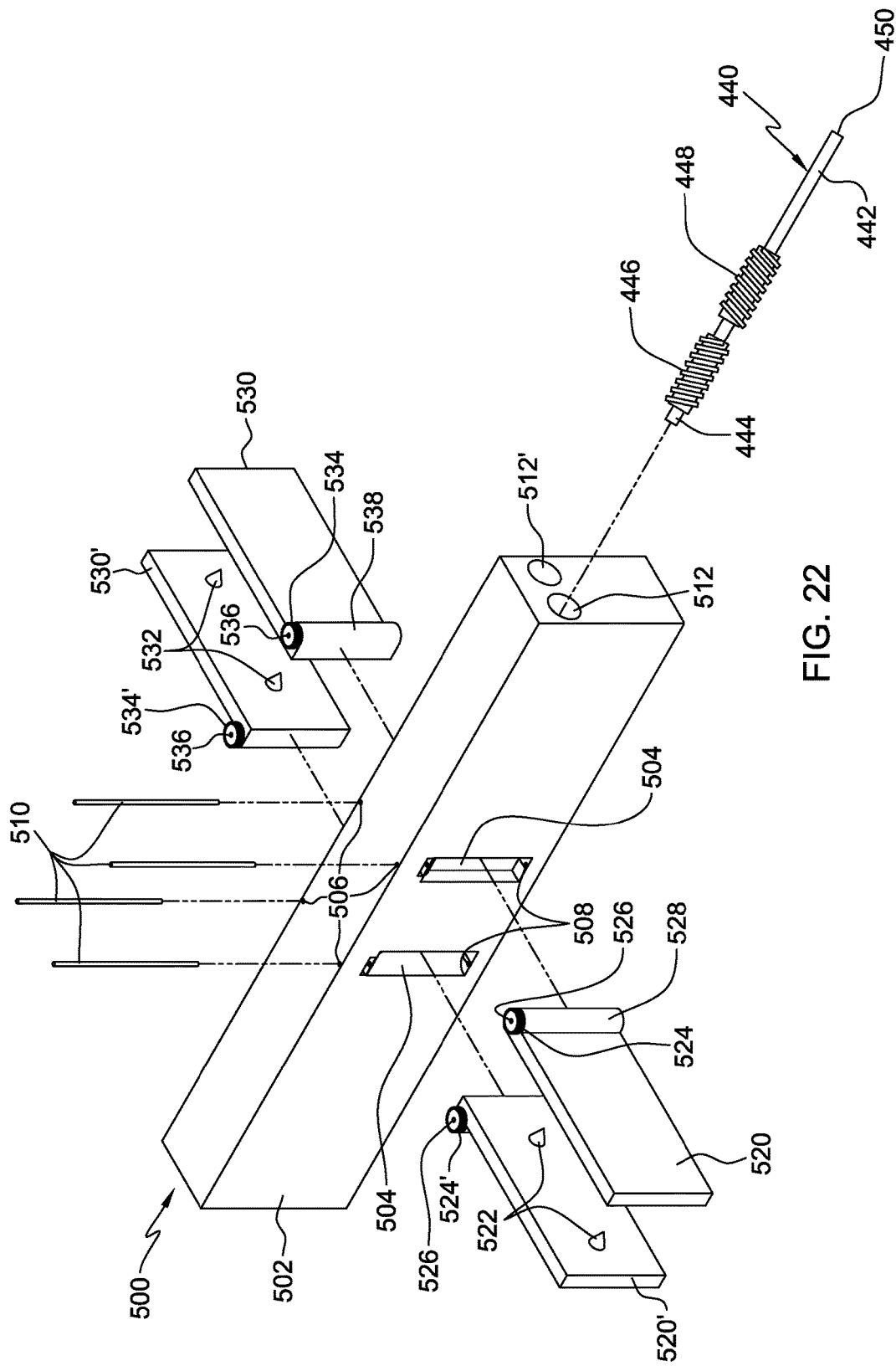
FIG. 22 is an exploded perspective view of the interspinous process device of FIG. 20, in accordance with an aspect of the present invention.

Another embodiment of an interspinous process device 500 is shown in FIGS. 20-23. The interspinous process device 500 may include a body 502, a first pair of moveable members 520, 520', and a second pair of moveable members 530, 530'. The body 502 may have, for example, a generally rectangular shape, however other cross-sectional geometries may be used. As shown in FIG. 22, the body 502 may include, for example, a plurality of slots 504. The plurality of slots 504 may include a first set of slots 504 on a first side of the body 502 and a second set of slots 504 (not shown) on a second side of the body 502 opposite the first side. The first side of the body 502 may be, for example, an inferior side and the second side of the body 502 may be, for example, a superior side. The plurality of slots 504 may be positioned, for example, near the center of the body 502. The body 502 may further include a plurality of first openings 506 engaging the slots 504 and, for example, extending from a front side of the body 502 or a posterior side of the patient into the slot 504. In addition, the body 502 may include a plurality of second openings 508 engaging the slots 504 and, for example, extending from the slot 504 toward a back side of the body 502 of an anterior side of the patient. The plurality of second openings 508 may, for example, only extend partially into the body 502 and may not be through holes such as the plurality of first openings 506. As shown in FIGS. 20-23, the body 502 may also include at least two cavities 512, 512'. The cavities 512, 512', may extend into the body 502 and may engage at least a portion of the plurality of slots 504. The device 500 may also include a plurality of pins 510 which may be sized to pass through the first openings 506, through the slots 504, and engage the second openings 508.

Figure 23:
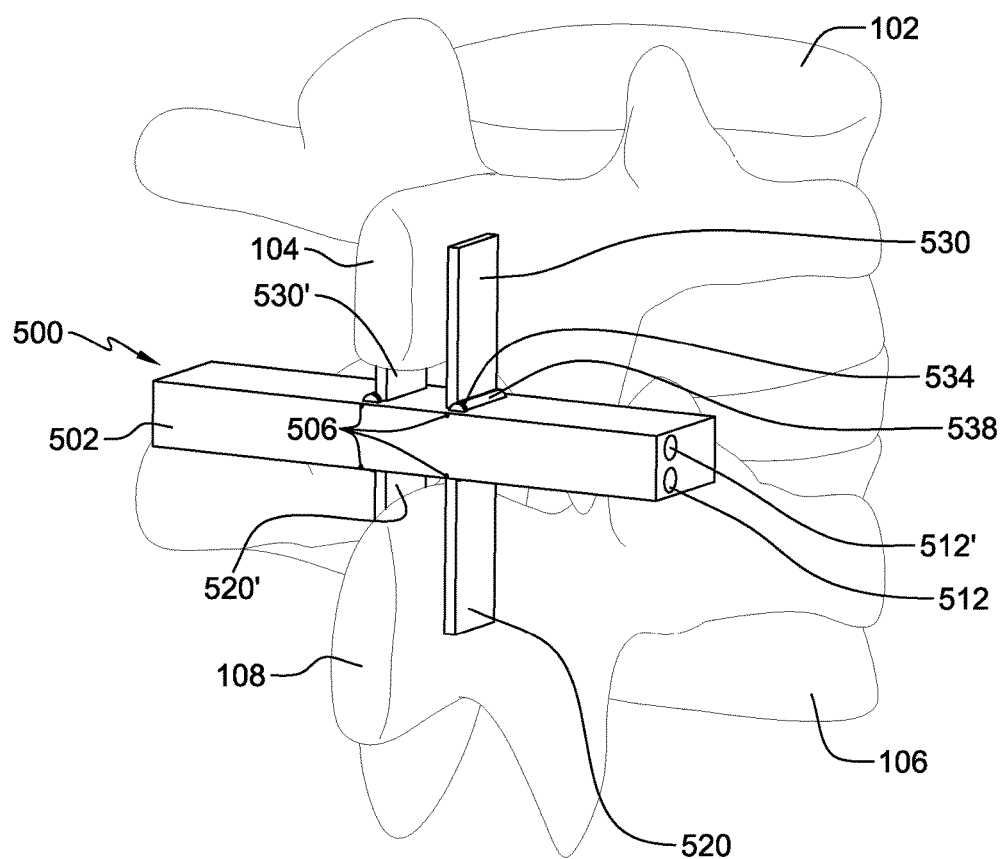
FIG. 23 is a posterior, lateral perspective view of a patient's spine showing the interspinous process device of FIG. 20 implanted in the patient's spine, in accordance with an aspect of the present invention.

The first pair of moveable members 520, 520' are shown in FIGS. 20-23. The first pair of moveable members 520, 520' may each include at least one engagement mechanism 522 on the surface that engages the spinous process 108. The at least one engagement mechanism 522 may be, for example, spikes, ridges, serrations, teeth, and other forms of coatings or textures that produce a rough surface for engaging with the spinous process 108 to assist with securing the moveable members 520, 520' to the spinous process 108. The moveable members 520, 520' may also include a boss 528 on a first end and an opening 526 extending through the boss 528 from the top surface to the bottom surface. The bosses 528 may be, for example, sized and shaped to be received within the slots 504 and may be, for example, relatively cylindrical to allow for the moveable members 520, 520' to pivotally move relative to the body 502. The openings 526 may be, for example, shaped and sized to receive a pin 510. The pin 510 may be used to secure the moveable members 520, 520' to the body 502 while allowing for the moveable members 520, 520' to rotate relative to the body 502 between an open and a closed position. The moveable members 520, 520' may also each include a movement mechanism 524, 524' positioned, for example, on a top or bottom surface of the cylindrical bosses 528. Alternatively, the movement mechanism 524, 524' may be positioned intermediate the bosses 528 between the first end and the second end of the bosses 528. The movement mechanism 524, 524' may include, for example, teeth, grooves, or gears (not shown) to engage an instrument, such as, the worm gear mechanism 440, as described in greater detail below, to deploy the moveable members 520, 520' from a retracted state to a deployed state. The first worm gear 446 of the worm gear mechanism 440 may couple to the movement mechanisms 524' and the second worm gear 448 may couple to the movement mechanisms 524. Then as the worm gear mechanism 440 is rotated the first and second worm gears 446, 448 rotate engaging the movement mechanisms 524', 524 to deploy or retract the moveable members 520', 520. When the moveable members 520, 520' are deployed, they may engage, for example, a spinous process 108, as shown in FIG. 23.

As shown in FIGS. 21-23, the second pair of moveable members 530, 530' may include at least one engagement mechanism 532 on the surface of the moveable members 530, 530' that engages a spinous process 104. The at least one engagement mechanism 532 may be of the type described above with reference to engagement mechanism 522 and will not be discussed again here for brevity sake. The moveable members 530, 530' may also include a boss 538 and an opening 536 of the type described above with reference to boss 528 and opening 526. Pins 510 may be used to secure the moveable members 530, 530' to the body 502 while allowing for the moveable members 530, 530' to rotate relative to the body 502 from an open to a closed position. The moveable members 530, 530' may also each include a movement mechanism 534, 534' of the type described above with reference to movement mechanisms 524, 524'. The movement mechanisms 534, 534' may engage an instrument, such as, worm gear mechanism 440, as described in greater detail below, to deploy the moveable members 530, 530'. The first worm gear 446 of the worm gear mechanism 440 may couple to the movement mechanisms 534' and the second worm gear 448 may couple to the movement mechanisms 534. Then as the worm gear mechanism 440 is rotated the first and second worm gears 446, 448 rotate engaging the movement mechanisms 534', 534 to deploy or retract the moveable members 530', 530. When the moveable members 530, 530' are deployed, they may engage, for example, a spinous process 104, as shown in FIG. 23.

As shown in FIG. 22, the device 500 may also include at least one worm gear mechanism 440 which may be inserted into the cavities 512, 512'. The at least one worm gear mechanism 440 is as described above with reference to device 400 and will not be described again here for brevity sake. In addition, device 500 may also include at least one locking mechanism 460, as described in greater detail above, to secure the at least one worm gear mechanism 440 in the desired position.

In another embodiment of the interspinous process device 500, the at least two cavities may be positioned on opposite ends of the body 502. A first cavity (not shown) may be positioned on a first end and engage at least a portion of two of the slots 504, for example, the slots 504 that receive the moveable members 520, 530. The second cavity (not shown) may be positioned on a second end and engage at least a portion of two of the slots 504, for example, the slots 504 that receive the moveable members 520', 530'. An alternative embodiment of the at least one worm gear mechanism 440 may be inserted into the first cavity to engage the movement mechanisms 524, 534 of the moveable members 520, 530. As the worm gear mechanism 440 is rotated, the worm gear mechanism 440 engages the movement mechanisms 524, 534 to deploy the moveable members 520, 530. The movement mechanisms 524, 534 may be positioned on the bosses 528, 538 to allow for the moveable members 520, 530 to be deployed simultaneously as the worm gear mechanism 440 is rotated within the first cavity. The worm gear mechanism 440 may be inserted into the second cavity to engage the movement mechanisms 524', 534' of the moveable members 520', 530'. As the worm gear mechanism 440 is rotated, the worm gear mechanism 440 engages the movement mechanisms 524', 534' to deploy the moveable members 520', 530'. The movement mechanisms 524', 534' may be positioned on the bosses 528, 538 to allow for the moveable members 520', 530' to be deployed simultaneously as the worm gear mechanism 440 is rotated within the second cavity.

In yet another embodiment of the interspinous process device 500, the body 502 may include one cavity positioned on a first end and extending along the longitudinal axis of the body 502, engaging at least a portion of each slot 504. Another alternative embodiment of the worm gear mechanism 440 may be inserted into the cavity to engage the movement mechanisms 524, 534 of the moveable members 520, 530. The worm gear mechanism 440 may then be rotated, engaging and rotating the movement mechanisms 524, 534 to deploy the moveable members 520, 530. The worm gear mechanism 440 may then be moved to engage the movement mechanisms 524', 534' of the moveable members 520', 530'. The worm gear mechanism 440 may then be rotated, engaging and rotating the movement mechanisms 524', 534' to deploy the moveable members 520', 530'. The movement mechanisms 524, 534 may be positioned on the bosses 528, 538 to allow for the moveable members 520, 530 to be deployed simultaneously as the worm gear mechanism 440 is rotated within the cavity. The movement mechanisms 524', 534' may be positioned on the bosses 528, 538 to allow for the moveable members 520', 530' to be deployed simultaneously as the worm gear mechanism 440 is rotated within the cavity.

Figure 26:
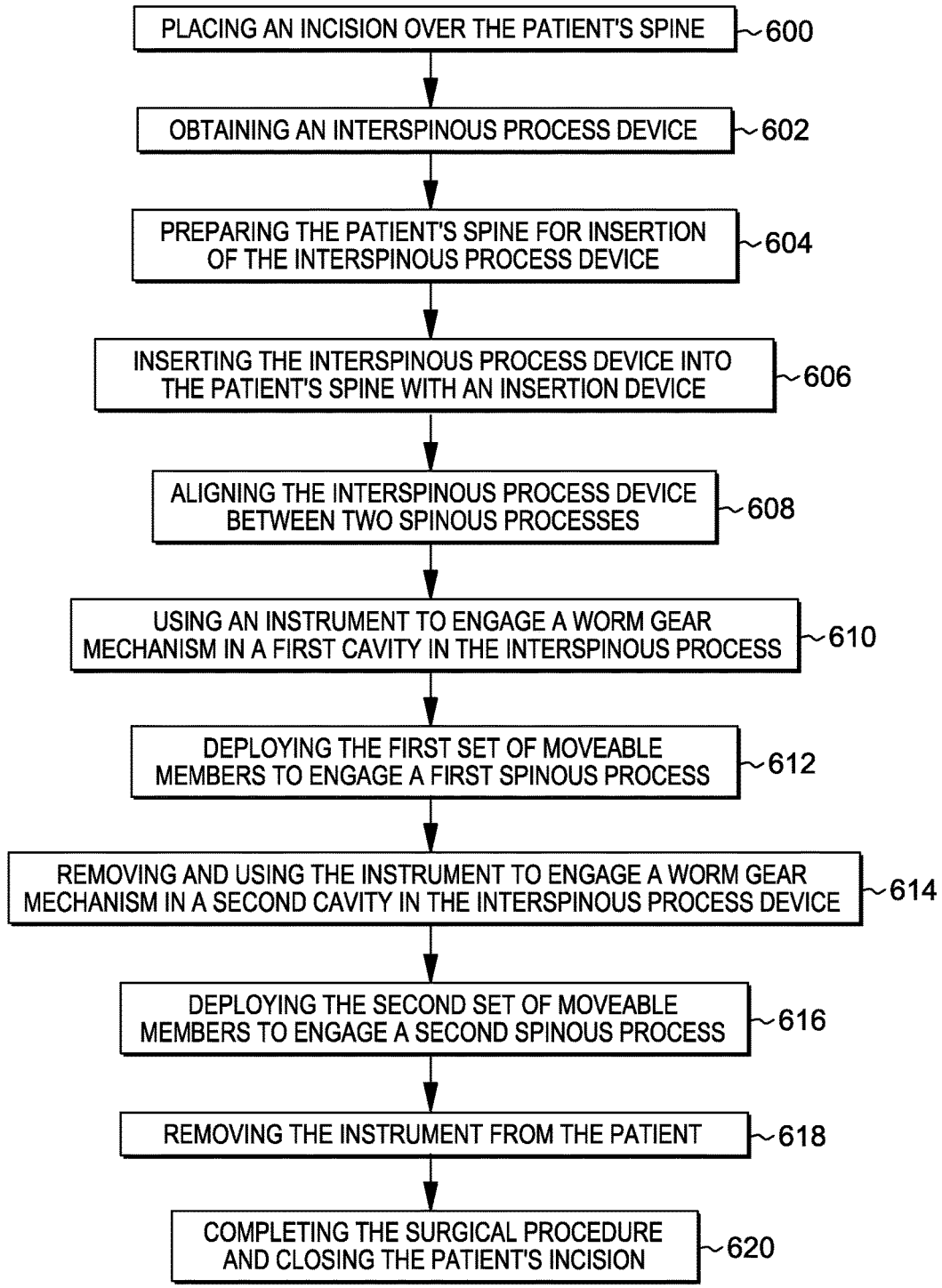
FIG. 26 depicts one embodiment of a method of using an interspinous process device, in accordance with an aspect of the present invention.

A method of using the spinous process devices 400, 500 in accordance with one or more aspects of the present invention is shown in FIG. 26. The method for using the spinous process devices 400, 500 may include, for instance: placing an incision over a patient's spine 600. The method may also include obtaining an interspinous process device 602 and preparing the patient's spine for insertion of the interspinous process device 604. The method may further include inserting the interspinous process device into the patient's spine with an insertion device 606 and aligning the interspinous process device between two adjacent spinous processes 608. In addition, the method may include using an instrument to engage a worm gear mechanism in a first cavity of the interspinous process device 610 and deploying a first set of moveable members to engage a first spinous process 612. The method may also include removing and using the instrument to engage a worm gear mechanism in a second cavity of the interspinous process device 614 and deploying a second set of moveable members to engage a second spinous process 616. The method may further include removing the instrument from the patient 618. Finally, the method may include completing the surgical procedure and closing the patient 620.

The method of using the spinous process devices 400, 500, as shown in FIG. 26, is described here in greater detail and also includes placing an incision over two spinous processes 104, 108 of a patient's spine. The incision may be positioned to allow for insertion, for example, posterolateral to the midline of the spine or obliquely. Then a dilator (not shown) may be inserted into the incision to access the interspinous process space between the two spinous processes 104, 108. The dilators may be, for example, an expandable dilator or a series of dilators, and they may be straight or curved. Next a reamer instrument, for example, reamer instrument 700 may be inserted to prepare the space for insertion of a spinous process device 400, 500. After the patient's spine is prepared, the spinous process device 400, 500 may be coupled to an insertion device for placement between two spinous processes 104, 108. Once a desired position of the device 400, 500 is achieved, then the moveable members 420, 420', 430, 430', 520, 520', 530 may be deployed to engage the spinous processes 104, 105.

The moveable members 420, 420', 430, 430', 520, 520', 530, 530' may be deployed, for example, by inserting an instrument into the cavities 412, 412', 512, 512' to engage the engagement opening 450 of a worm gear mechanism 440. The instrument may be, for example, a screw driver or drill. For example, the instrument may be inserted into a first cavity 412 to engage the engagement opening 450, then the instrument may be rotated in a first direction to rotate the worm gear mechanism 440. As the worm gear mechanism 440 rotates, the first worm gear 446 and second worm gear 448 also rotate. Since the first and second worm gears 446, 448 are positioned to engage the movement mechanisms 424', 424, respectively, as the worm gears 446, 448 rotate, the aligned movement mechanisms 424', 424 also rotate to deploy the moveable members 420, 420'.

Next, the instrument may be removed from the first cavity 412 and inserted into a second cavity 412' to engage the engagement opening 450 of the worm gear mechanism 440 in the second cavity 412'. The instrument may be rotated in a first direction to turn the worm gear mechanism 400. As described in greater detail above, as the worm gear mechanism 440 is rotated the first and second worm gears 446, 448 rotate and in turn rotate the movement mechanisms 434', 434, respectively to deploy the moveable members 430, 430'. Where both worm gear mechanisms 400 are identical the direction of rotation may be, for example, counterclockwise or clockwise, for example, in the depicted embodiment, the direction is counterclockwise. In another embodiment, if the worm gear mechanism 400 in the first cavity 412 includes a first left hand worm gear 446 and a second right hand worm gear 448 and the worm gear mechanism 400 in the second cavity 412' includes a first right hand worm gear 446 and a second left hand worm gear 448, then the worm gear mechanism 400 in the first cavity 412 may be rotated clockwise and the worm gear mechanism 400 in the second cavity 412' may be rotated counterclockwise. Alternative mechanisms that accomplish the same or similar function may be used in place of worm gear mechanism 440 to deploy the moveable members 420, 420', 430, 430'.

The moveable members 520, 520', 530, 530' of device 500 may also be deployed as described above with reference to device 400, which will not be described again here for brevity sake.

After the moveable members are deployed, the instrument may be removed from the patient. Then a compression device (not shown) may be used to lock the device 400, 500 to ensure that the device 400, 500 is firmly grasping the spinous processes 104, 108. Next the insertion device may be removed from the patient and the surgical procedure may be completed. Finally, the patient's incision may be closed.

Figure 27:
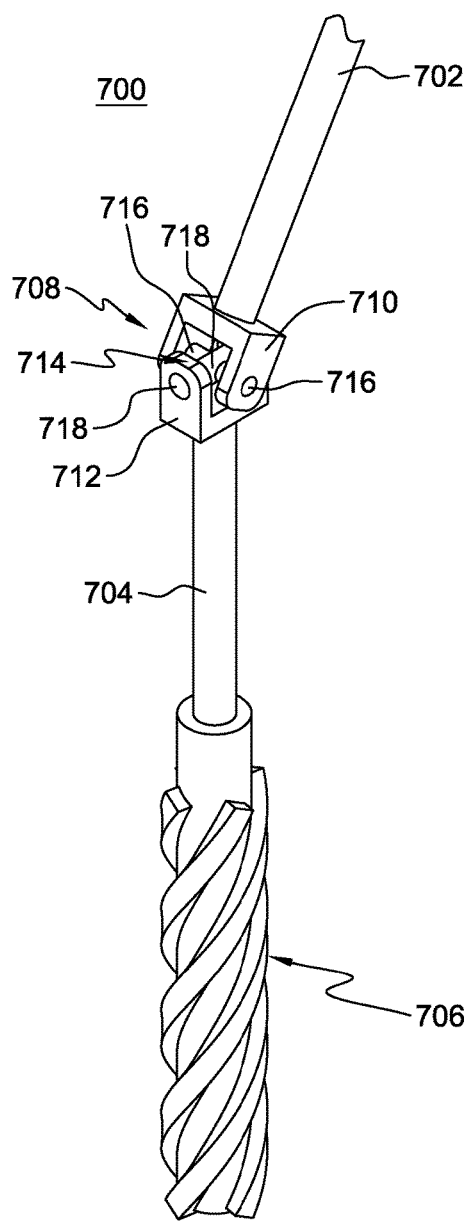
FIG. 27 is a perspective view of a reamer instrument in a first position, in accordance with an aspect of the present invention.
Figure 28:
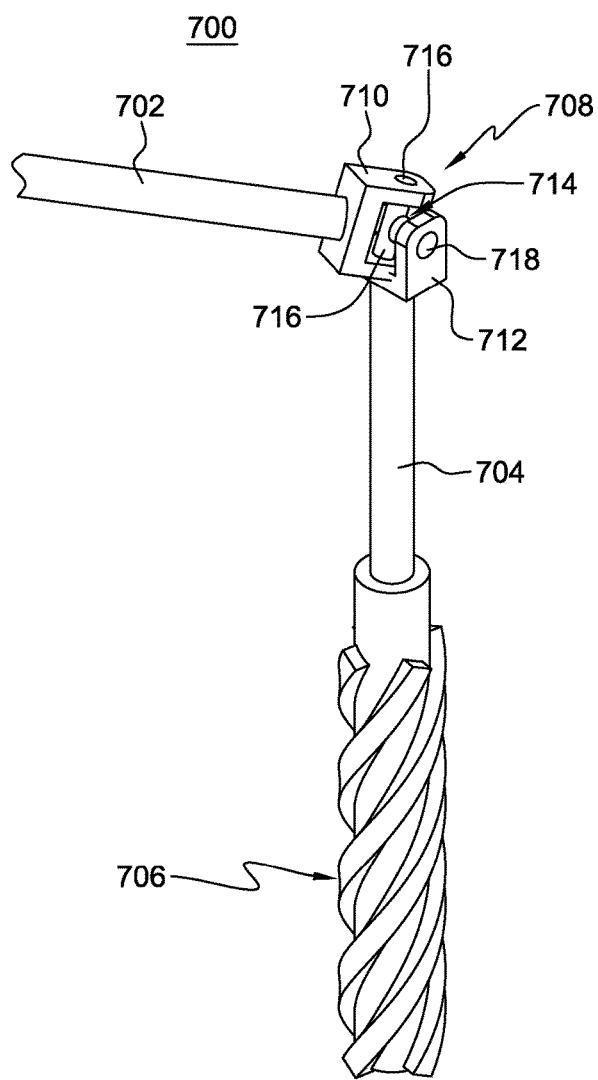
FIG. 28 is a perspective view of the reamer instrument of FIG. 27 in a second position, in accordance with an aspect of the present invention.

A reamer instrument 700 is shown in FIGS. 27-28. The reamer instrument 700 may include a first shaft 702 coupled to a second shaft 704 by a joint 708. The first shaft 702 may include an attachment portion (not shown) on a first end for engagement with a drill and may be coupled to the joint 708 on the second end. The second shaft 704 may be coupled to the joint 708 on a first end and may include a reamer portion 706 on the second end. The joint 708 may include a first body 710, a second body 712, and a hinge member 714 moveably coupling the first body 710 and second body 712. The first body 710 may be attached to the second end of the first shaft 702 and the second body 712 may be attached to the first end of the second shaft 704. The hinge member 714 may include a first pin 716 and a second pin 718 which are coupled together to form the hinge member 714. The first pin 716 may be positioned perpendicular to the second pin 718. The first pin 716 may engage the first body 710 and the second pin 718 may engage the second body 712 to enable the second shaft 704 to be positioned at any angle relative to the first shaft 702 as the reamer portion 706 is drilled into a patient's bones.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. A spinous process fixation device, comprising:
    a first attachment portion comprising:
        a first member; and
        a second member configured to couple to the first member;
    a second attachment portion engaging the first attachment portion, the second attachment portion comprising:
        a third member; and
        a fourth member configured to couple to the third member;
    wherein the first attachment portion and the second attachment portion are positioned to couple to at least two spinous processes;
    wherein the first member comprises:
        a body;
        an engagement member;
        a plurality of teeth positioned on the engagement member; and
        a slot positioned on an exterior surface of the body and extending from a first side to a second side of the body,
    wherein the second member includes comprises:
        a body; and
        an engagement portion, and the engagement member of the first member couples to the engagement portion of the second member; and
    wherein the third member comprises:
        a body;
        an engagement member; and
        a protrusion extending away from an interior surface of the body and extending from a first side to a second side,
        wherein the protrusion of the third member engages the slot of the first member when the first attachment portion couples to the second attachment portion,
    wherein the fourth member comprises:
        a body; and
        an engagement portion, and
        wherein the engagement member of the third member couples to the engagement portion of the fourth member.

2. The spinous process fixation device of claim 1, wherein the first member further comprises:
    at least one protuberance on an interior surface of the body positioned between a top of the body and the engagement member.

3. The spinous process fixation device of claim 2, wherein the engagement portion of the second member comprises:
    a first engagement segment; and
    a second engagement segment positioned parallel to and spaced apart from the first engagement segment to form a channel, the channel sized to receive the engagement member of the first member; and
    wherein the second member further comprises:
        a plurality of first teeth positioned on an inner surface of the first engagement segment in the channel;
        a plurality of second teeth positioned on an inner surface of the second engagement segment in the channel, wherein the plurality of teeth on the engagement member of the first member engage the plurality of first teeth and the plurality of second teeth of the engagement portion of the second member;
        a slot positioned on an exterior surface of the body and extending from a first side to a second side of the body; and
        at least one protuberance on an interior surface of the body positioned between a top of the body and the engagement portion.

4. The spinous process fixation device of claim 3, wherein the third member further comprises:
    a plurality of teeth positioned on the engagement member; and
    at least one protuberance on the interior surface of the body positioned between the engagement member and a bottom of the body.

5. The spinous process fixation device of claim 4, wherein the engagement portion of the fourth member comprises:

a first engagement segment; and
a second engagement segment positioned parallel to and spaced apart from the first engagement segment to form a channel, wherein the channel is sized to receive the engagement member of the third member; and
wherein the second member further comprises:
a plurality of first teeth positioned on an inner surface of the first engagement segment in the channel;
a plurality of second teeth positioned on an inner surface of the second engagement segment in the channel, wherein the plurality of teeth on the engagement member of the third member engage the plurality of first teeth and the plurality of second teeth of the engagement portion of the fourth member;
a protrusion extending away from an interior surface of the body and extending from a first side to a second side; and
at least one protuberance on the interior surface of the body positioned between the engagement portion and a bottom of the body.

6. The spinous process fixation device of claim 5, wherein the protrusion of the fourth member engages the slot of the second member.

7. The spinous process fixation device of claim 1, wherein the engagement member is angled relative to the body.

8. The spinous process fixation device of claim 1, wherein the engagement member extends normal to the interior surface of the body.

9. The spinous process fixation device of claim 1, wherein the engagement portion is angled relative to the body.

10. The spinous process fixation device of claim 3, wherein the engagement portion is normal to the interior surface of the body.

11. A spinous process fixation system, comprising:
a spinous process fixation device comprising:
a first attachment portion comprising:
a first member; and
a second member configured to couple to the first member;
a second attachment portion engaging the first attachment portion, the second attachment portion comprising:
a third member; and
a fourth member configured to couple to the third member;
wherein the first attachment portion and the second attachment portion are positioned to couple at least two spinous processes; and
an insertion instrument configured for engagement with the spinous process fixation device, wherein the insertion instrument comprises:
a first member with a handle portion and an engagement portion;
a second member with a handle portion and an engagement portion; and
a pivot point moveably coupling the first member and the second member;
wherein the engagement portion of the first member comprises:
a body;
a first groove extending along a longitudinal axis of a bottom surface of the body; and
a second groove extending perpendicular to the first groove from a medial side of the body to intersect the first groove;
wherein the engagement portion of the second member comprises:
a body;
a first groove extending along a longitudinal axis of a bottom surface of the body; and
a second groove extending perpendicular to the first groove from a medial side of the body to intersect the first groove.

12. The spinous process fixation system of claim 11, wherein the first groove of the first member of the insertion instrument engages the body of the first member of the spinous process fixation device, the second groove of the first member of the insertion instrument engages the engagement member of the first member of the spinous process fixation device, the first groove of the second member of the insertion instrument engages the body of the second member of the spinous process fixation device, and the second groove of the second member of the insertion instrument engages the engagement portion of the second member of the spinous process fixation device.

13. The spinous process fixation system of claim 11, wherein the first groove of the first member of the insertion instrument engages the body of the third member of the spinous process fixation device, the second groove of the first member of the insertion instrument engages the engagement member of the third member of the spinous process fixation device, the first groove of the second member of the insertion instrument engages the body of the fourth member of the spinous process fixation device, and the second groove of the second member of the insertion instrument engages the engagement portion of the fourth member of the spinous process fixation device.

14. A spinous process fixation assembly, comprising:
a first member having an engagement member coupled to and extending away from an interior surface of the first member;
a second member having an engagement portion coupled to and extending away from an interior surface of the second member;
a third member having an engagement member coupled to and extending away from an interior surface of the third member; and
a fourth member having an engagement portion coupled to and extending away from an interior surface of the fourth member;
wherein the engagement member of the first member connects to the engagement portion of the second member and the engagement member of the third member connects to the engagement portion of the fourth member to form a spinous process fixation assembly;
wherein the interior surface of the third member engages an exterior surface of the first member and the interior surface of the fourth member engages an exterior surface of the second member to form the spinous process fixation assembly.

15. The spinous process fixation assembly of claim 14, further comprising a first attachment portion comprising the first member connected to the second member, wherein the first member is positioned parallel to the second member when assembled.

16. The spinous process fixation assembly of claim 14, further comprising a second attachment portion comprising the third member connected to the fourth member, wherein the third member is positioned parallel to the fourth member when assembled.

* * * * *

UNITED STATES PATENT AND TRADEMARK OFFICE
CERTIFICATE OF CORRECTION

PATENT NO. : 10,213,234 B2
APPLICATION NO. : 15/264099
DATED : February 26, 2019
INVENTOR(S) : Fessler et al.

Page 1 of 1

It is certified that error appears in the above-identified patent and that said Letters Patent is hereby corrected as shown below:

In the Claims

Column 18, Line 12: Claim 1, Delete "includes"

Signed and Sealed this
Sixteenth Day of April, 2019

Andrei Iancu
*Director of the United States Patent and Trademark Office*